US012779018B2

(12) United States Patent
Lee et al.

(10) Patent No.: US 12,779,018 B2
(45) Date of Patent: Nov. 3, 2026

(54) PHARMACEUTICAL COMPOSITION FOR PREVENTING OR TREATING BONE DISEASES, COMPRISING TRIPLE AGONIST OR CONJUGATE THEREOF HAVING ACTIVITY WITH RESPECT TO ALL OF GLUCAGON, GLP-1 AND GLP RECEPTORS

(71) Applicant: HANMI PHARM. CO., LTD., Hwaseong-si (KR)

(72) Inventors: Jong Suk Lee, Hwaseong-si (KR); Sang Don Lee, Hwaseong-si (KR); Sang Hyun Lee, Hwaseong-si (KR)

(73) Assignee: HANMI PHARM. CO., LTD., Hwaseong-si (KR)

( * ) Notice: Subject to any disclaimer, the term of this patent is extended or adjusted under 35 U.S.C. 154(b) by 699 days.

(21) Appl. No.: 18/028,424

(22) PCT Filed: Sep. 24, 2021

(86) PCT No.: PCT/KR2021/013007

§ 371 (c)(1),
(2) Date: Mar. 24, 2023

(87) PCT Pub. No.: WO2022/065898

PCT Pub. Date: Mar. 31, 2022

(65) Prior Publication Data

US 2023/0355720 A1 Nov. 9, 2023

(30) Foreign Application Priority Data

Sep. 25, 2020 (KR) ........................ 10-2020-0125196

(51) Int. Cl.

| | |
|---|---|
| ***A61K 38/26*** | (2006.01) |
| ***A61K 38/16*** | (2006.01) |
| ***A61K 47/60*** | (2017.01) |
| ***A61K 47/68*** | (2017.01) |
| ***A61P 19/08*** | (2006.01) |
| ***A61P 19/10*** | (2006.01) |

(52) U.S. Cl.

CPC .............. *A61K 38/26* (2013.01); *A61K 38/16* (2013.01); *A61K 47/60* (2017.08); *A61K 47/6811* (2017.08); *A61P 19/08* (2018.01); *A61P 19/10* (2018.01)

(58) Field of Classification Search

CPC ........ A61K 38/16; A61K 38/26; A61K 47/60; A61K 47/68

See application file for complete search history.

(56) References Cited

U.S. PATENT DOCUMENTS

| | | | | |
|---|---|---|---|---|
| 2016/0257729 | A1 | 9/2016 | Just et al. | |
| 2018/0311315 | A1* | 11/2018 | Oh ........................ | C07K 14/47 |

FOREIGN PATENT DOCUMENTS

| | | | |
|---|---|---|---|
| CN | 109071624 | A | 12/2018 |
| JP | 2017-512800 | A | 5/2017 |
| KR | 10-2017-0080522 | A | 7/2017 |
| WO | 96/32478 | A1 | 10/1996 |
| WO | 97/34631 | A1 | 9/1997 |
| WO | 02/24214 | A2 | 3/2002 |
| WO | 2017/116204 | A1 | 7/2017 |
| WO | 2017/116205 | A1 | 7/2017 |
| WO | 2020130749 | A1 | 6/2020 |

OTHER PUBLICATIONS

Jackuliak et al., Int. J. Endocrinol., vol. 2014, Article ID 820615, 10 pages.*

Gupta et al., CNS Drugs, 2014, vol. 28:731-742.*

Mabilleau et al., "Incretin-based therapy for the treatment of bone fragility in diabetes mellitus" Peptides, vol. 100, 2018, pp. 108-113.

Mansur et al., "A new stable GIP-Oxyntomodulin hybrid peptide improved bone strength both at the organ and tissue levels in genetically-inherited type 2 diabetes mellitus", Bone, vol. 87, 2016, pp. 102-113.

Hansen et al., "Effects of gastric inhibitory polypeptide, glucagon-like peptide-1 and glucagon-like Peptide-1 receptor agonists on Bone Cell Metabolism", Basic & Clinical Pharmacology & Toxicology, vol. 122, 2018, pp. 25-37.

Extended European Search Report issued Oct. 22, 2024 in application No. 21872926.7.

Sangdon Lee, et al., "Bone Protective Effect of a Novel Long-Acting GLP-1/GIP/Glucagon Triple Agonist (HM15211) in an Animal Model", Diabetes, 2018, vol. 67, Supplement 1, https://doi.org/10.2337/db18-1105-P.

Jacques P. Brown, MD, et al., "Bisphosphonates for treatment of osteoporosis", Expected benefits, potential harms, and drug holidays, Clinical Review, Canadian Family Physician, Apr. 2014, pp. 324-333, vol. 60(4).

International Search Report for PCT/KR2021/013007 dated Jan. 10, 2022.

Schiellerup et al., "Gut Hormones and Their Effect on Bone Metabolism. Potential Drug Therapies in Future Osteoporosis Treatment", Frontiers in Endocrinology, vol. 10, Article 75, 2019, pp. 1-13.

Communication dated Jul. 16, 2026, issued in Chinese Application No. 202180072841.1.

Qian et al., "Research Progress on Multi-receptor Agonists Based on Glucagon-like Peptide-1", Progress in Pharmaceutical Sciences, 2019, vol. 43, No. 10, pp. 738-748.

* cited by examiner

*Primary Examiner* — Xiaozhen Xie

(74) *Attorney, Agent, or Firm* — Sughrue Mion, PLLC

(57) ABSTRACT

A therapeutic use of a triple agonist and/or a long-acting conjugate thereof having activity with respect to all of glucagon, glucagon-like peptide-1 (GLP-1) and glucose-dependent insulinotropic polypeptide (GIP) receptors is disclosed. The triple agonist and/or the long-acting conjugate thereof can significantly reduce symptoms of bone diseases, and enhance patient convenience through a dramatic increase in blood half-life and long-acting in-vivo effects.

17 Claims, 5 Drawing Sheets

Specification includes a Sequence Listing.

[FIG. 1]
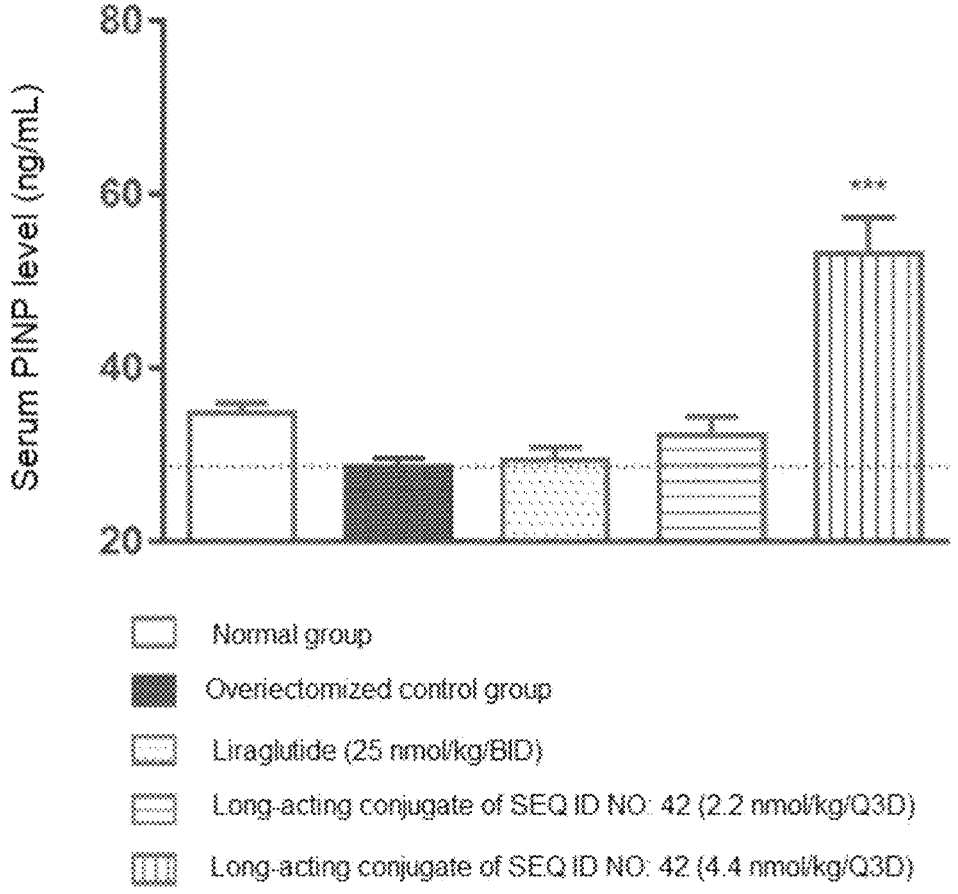

[FIG. 2]
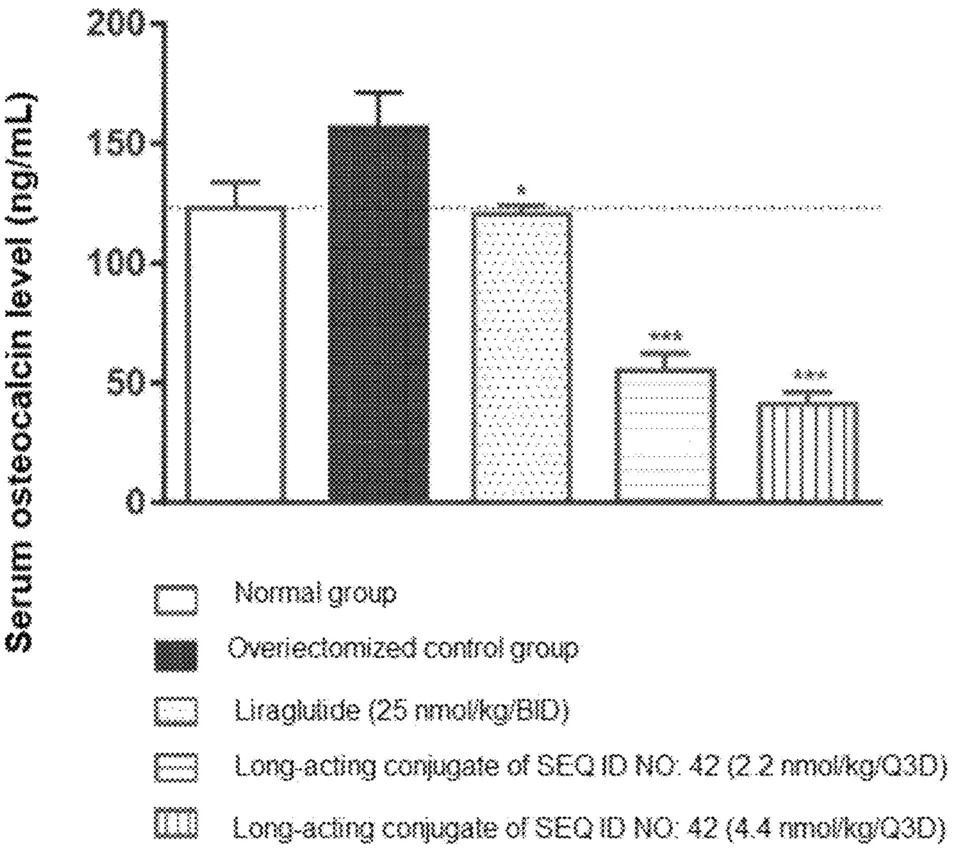

[FIG. 3]
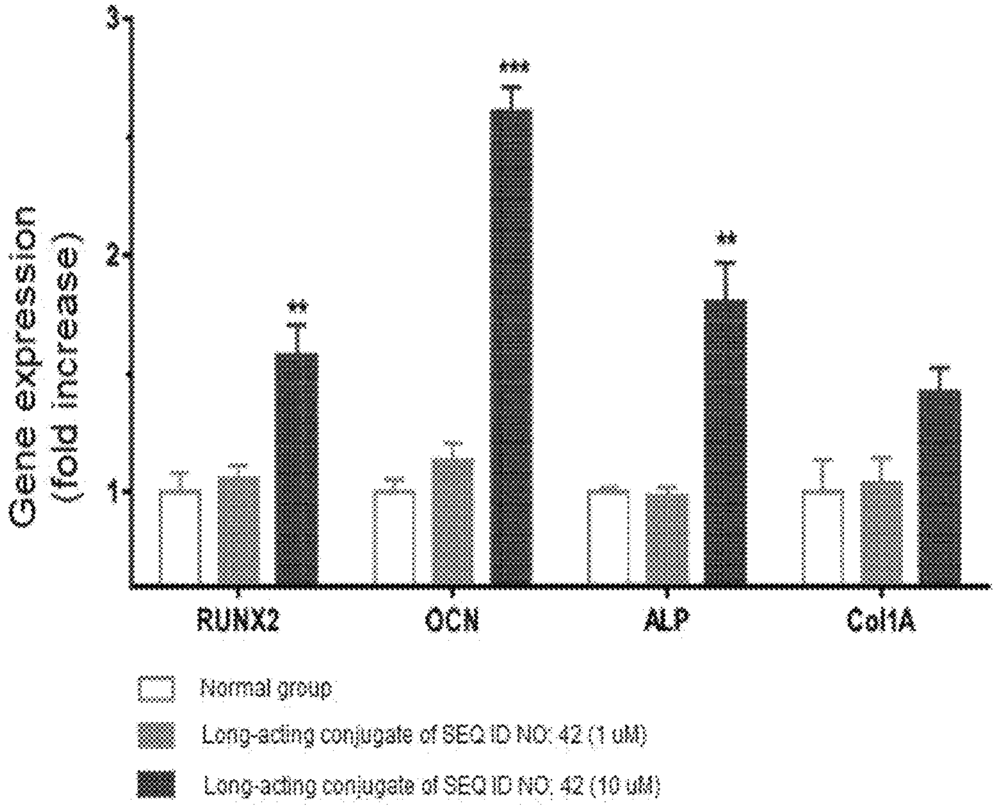

[FIG. 4]
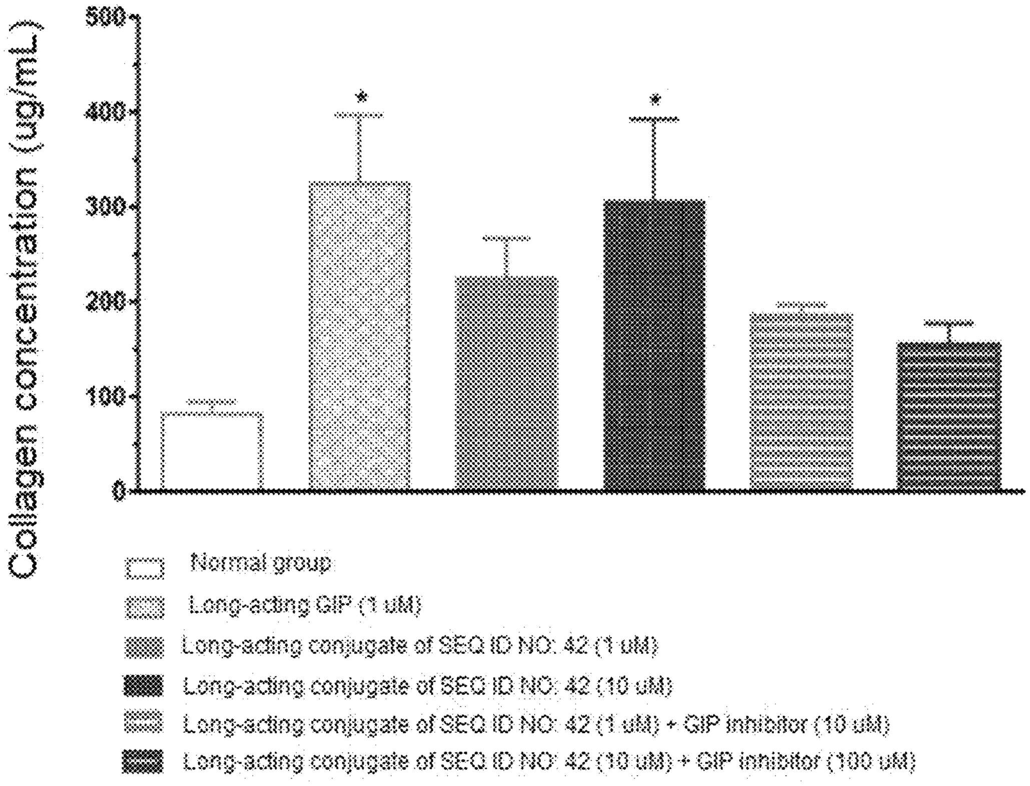

[FIG. 5]
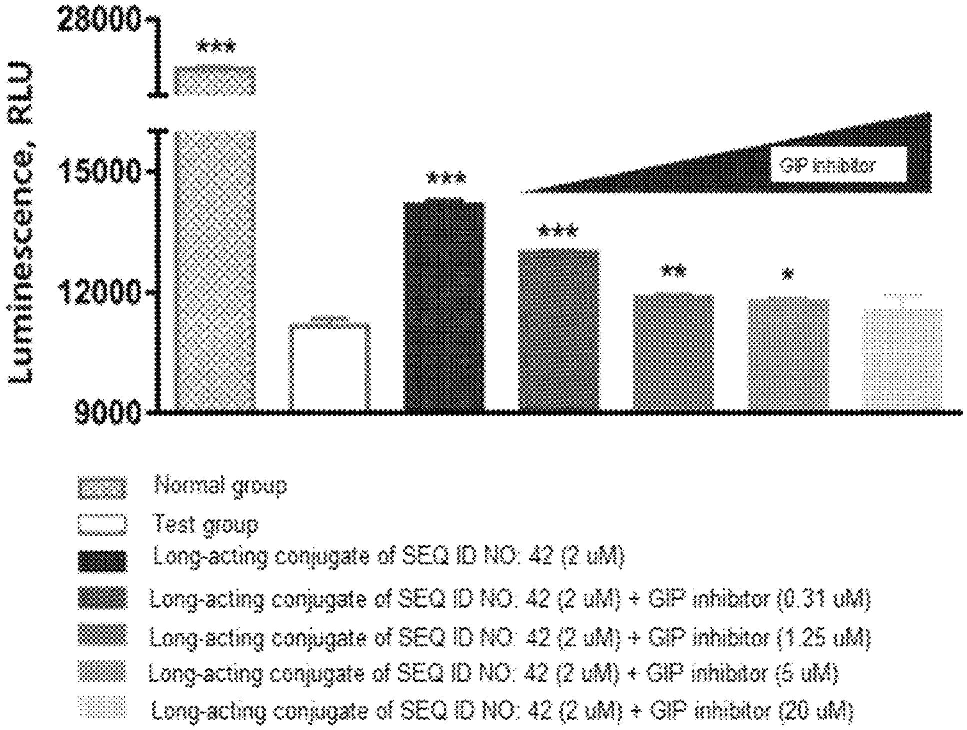

```
                         SEQUENCE LISTING


<160> NUMBER OF SEQ ID NOS: 134

<210> SEQ ID NO 1
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)

<400> SEQUENCE: 1

His Xaa Gln Gly Thr Phe Thr Ser Asp Val Ser Ser Tyr Leu Asp Gly
1               5                   10                  15

Gln Ala Ala Lys Glu Phe Ile Ala Trp Leu Val Lys Gly Cys
            20                  25                  30
```

```
<210> SEQ ID NO 2
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)

<400> SEQUENCE: 2

His Xaa Gln Gly Thr Phe Thr Ser Asp Val Ser Ser Tyr Leu Asp Gly
1               5                   10                  15

Gln Ala Gln Lys Glu Phe Ile Ala Trp Leu Val Lys Gly Cys
            20                  25                  30


<210> SEQ ID NO 3
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)

<400> SEQUENCE: 3

His Xaa Gln Gly Thr Phe Thr Ser Asp Val Ser Ser Tyr Leu Leu Gly
1               5                   10                  15

Gln Ala Ala Lys Gln Phe Ile Ala Trp Leu Val Lys Gly Gly Gly Pro
            20                  25                  30

Ser Ser Gly Ala Pro Pro Pro Ser Cys
        35                  40


<210> SEQ ID NO 4
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)

<400> SEQUENCE: 4

His Xaa Gln Gly Thr Phe Thr Ser Asp Val Ser Ser Tyr Leu Leu Gly
1               5                   10                  15

Gln Gln Gln Lys Glu Phe Ile Ala Trp Leu Val Lys Gly Cys
            20                  25                  30


<210> SEQ ID NO 5
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
```

<400> SEQUENCE: 5

His Xaa Gln Gly Thr Phe Thr Ser Asp Val Ser Ser Tyr Leu Leu Gly
1 5 10 15

Gln Gln Gln Lys Glu Phe Ile Ala Trp Leu Val Lys Gly Gly Gly Pro
20 25 30

Ser Ser Gly Ala Pro Pro Pro Ser Cys
35 40

<210> SEQ ID NO 6
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)

<400> SEQUENCE: 6

His Xaa Gln Gly Thr Phe Thr Ser Asp Val Ser Ser Tyr Leu Asp Gly
1 5 10 15

Gln Ala Ala Lys Glu Phe Val Ala Trp Leu Leu Lys Gly Cys
20 25 30

<210> SEQ ID NO 7
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)

<400> SEQUENCE: 7

His Xaa Gln Gly Thr Phe Thr Ser Asp Val Ser Lys Tyr Leu Asp Gly
1 5 10 15

Gln Ala Ala Lys Glu Phe Val Ala Trp Leu Leu Lys Gly Cys
20 25 30

<210> SEQ ID NO 8
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)

<400> SEQUENCE: 8

His Xaa Gln Gly Thr Phe Thr Ser Asp Val Ser Lys Tyr Leu Asp Gly
1 5 10 15

Gln Ala Ala Gln Glu Phe Val Ala Trp Leu Leu Lys Gly Cys
20 25 30

<210> SEQ ID NO 9
<211> LENGTH: 30
<212> TYPE: PRT
<213> ORGANISM: Artificial Sequence
<220> FEATURE:
<223> OTHER INFORMATION: Trigonal agonist

```
<220> FEATURE:
<221> NAME/KEY: MISC_FEATURE
<222> LOCATION: (2)
<223> OTHER INFORMATION: Xaa is 2-aminoisobutyric acid (Aib)

<400> SEQUENCE: 9

His Xaa Gln Gly Thr Phe Thr Ser Asp Val Ser Lys Tyr Leu Asp Gly
1               5                   10                  15

Gln Ala Ala Gln Glu Phe Val Ala Trp Leu Leu Ala Gly Cys
            20                  25                  30


<210> SEQ ID NO 10
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)

<400> SEQUENCE: 10

His Xaa Gln Gly Thr Phe Thr Ser Asp Val Ser Lys Tyr Leu Asp Gly
1               5                   10                  15

Gln Ala Ala Gln Glu Phe Val Ala Trp Leu Leu Ala Gly Gly Gly Pro
            20                  25                  30

Ser Ser Gly Ala Pro Pro Pro Ser Cys
        35                  40


<210> SEQ ID NO 11
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)

<400> SEQUENCE: 11

Xaa Gly Glu Gly Thr Phe Thr Ser Asp Leu Ser Lys Tyr Leu Asp Ser
1               5                   10                  15

Arg Arg Gln Gln Leu Phe Val Gln Trp Leu Lys Ala Gly Gly Pro Ser
            20                  25                  30

Ser Gly Ala Pro Pro Pro Ser His Gly
        35                  40


<210> SEQ ID NO 12
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)

<400> SEQUENCE: 12

Xaa Gly Glu Gly Thr Phe Ile Ser Asp Leu Ser Lys Tyr Met Asp Glu
1               5                   10                  15

Gln Ala Val Gln Leu Phe Val Glu Trp Leu Met Ala Gly Gly Pro Ser
            20                  25                  30
```

-continued

Ser Gly Ala Pro Pro Pro Ser His Gly
35 40

<210> SEQ ID NO 13
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)

<400> SEQUENCE: 13

Xaa Gly Glu Gly Thr Phe Ile Ser Asp Tyr Ser Ile Gln Leu Asp Glu
1 5 10 15

Ile Ala Val Gln Asp Phe Val Glu Trp Leu Leu Ala Gln Lys Pro Ser
20 25 30

Ser Gly Ala Pro Pro Pro Ser His Gly
35 40

<210> SEQ ID NO 14
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)

<400> SEQUENCE: 14

Xaa Gly Gln Gly Thr Phe Thr Ser Asp Tyr Ser Ile Gln Leu Asp Glu
1 5 10 15

Ile Ala Val Arg Asp Phe Val Glu Trp Leu Lys Asn Gly Gly Pro Ser
20 25 30

Ser Gly Ala Pro Pro Pro Ser His Gly
35 40

<210> SEQ ID NO 15
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)

<400> SEQUENCE: 15

Xaa Gly Gln Gly Thr Phe Thr Ser Asp Leu Ser Lys Gln Met Asp Glu
1 5 10 15

Glu Ala Val Arg Leu Phe Ile Glu Trp Leu Lys Asn Gly Gly Pro Ser
20 25 30

Ser Gly Ala Pro Pro Pro Ser His Gly
35 40

<210> SEQ ID NO 16
<211> LENGTH: 41
<212> TYPE: PRT
<213> ORGANISM: Artificial Sequence
<220> FEATURE:
<223> OTHER INFORMATION: Trigonal agonist

```
<220> FEATURE:
<221> NAME/KEY: MISC_FEATURE
<222> LOCATION: (1)
<223> OTHER INFORMATION: Xaa is 4-imidazoacetyl (CA)

<400> SEQUENCE: 16

Xaa Gly Gln Gly Thr Phe Thr Ser Asp Leu Ser Lys Gln Met Asp Ser
1               5                   10                  15

Glu Ala Gln Gln Leu Phe Ile Glu Trp Leu Lys Asn Gly Gly Pro Ser
            20                  25                  30

Ser Gly Ala Pro Pro Pro Ser His Gly
        35                  40


<210> SEQ ID NO 17
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)

<400> SEQUENCE: 17

Xaa Gly Gln Gly Thr Phe Thr Ser Asp Leu Ser Lys Gln Met Asp Glu
1               5                   10                  15

Glu Arg Ala Arg Glu Phe Ile Glu Trp Leu Leu Ala Gln Lys Pro Ser
            20                  25                  30

Ser Gly Ala Pro Pro Pro Ser His Gly
        35                  40


<210> SEQ ID NO 18
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)

<400> SEQUENCE: 18

Xaa Gly Gln Gly Thr Phe Thr Ser Asp Leu Ser Lys Gln Met Asp Ser
1               5                   10                  15

Glu Arg Ala Arg Glu Phe Ile Glu Trp Leu Lys Asn Thr Gly Pro Ser
            20                  25                  30

Ser Gly Ala Pro Pro Pro Ser His Gly
        35                  40


<210> SEQ ID NO 19
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)

<400> SEQUENCE: 19

Xaa Gly Gln Gly Thr Phe Thr Ser Asp Leu Ser Ile Gln Tyr Asp Ser
1               5                   10                  15
```

-continued

Glu His Gln Arg Asp Phe Ile Glu Trp Leu Lys Asp Thr Gly Pro Ser
            20                  25                  30

Ser Gly Ala Pro Pro Pro Ser His Gly
        35                  40

<210> SEQ ID NO 20
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)

<400> SEQUENCE: 20

Xaa Gly Gln Gly Thr Phe Thr Ser Asp Leu Ser Ile Gln Tyr Glu Glu
1               5                   10                  15

Glu Ala Gln Gln Asp Phe Val Glu Trp Leu Lys Asp Thr Gly Pro Ser
            20                  25                  30

Ser Gly Ala Pro Pro Pro Ser His Gly
        35                  40

<210> SEQ ID NO 21
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 21

Tyr Xaa Gln Gly Thr Phe Thr Ser Asp Tyr Ser Lys Tyr Leu Asp Glu
1               5                   10                  15

Cys Arg Ala Lys Glu Phe Val Gln Trp Leu Leu Asp His His Pro Ser
            20                  25                  30

Ser Gly Gln Pro Pro Pro Ser
        35

<210> SEQ ID NO 22
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 22

Tyr Xaa Gln Gly Thr Phe Thr Ser Asp Tyr Ser Lys Cys Leu Asp Glu
1               5                   10                  15

Lys Arg Ala Lys Glu Phe Val Gln Trp Leu Leu Asp His His Pro Ser
            20                  25                  30

Ser Gly Gln Pro Pro Pro Ser
        35

<210> SEQ ID NO 23
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 23

Tyr Xaa Gln Gly Thr Phe Thr Ser Asp Tyr Ser Lys Tyr Leu Asp Glu
1               5                   10                  15

Cys Arg Ala Lys Glu Phe Val Gln Trp Leu Leu Ala Gln Lys Gly Lys
            20                  25                  30

Lys Asn Asp Trp Lys His Asn Ile Thr
        35                  40

<210> SEQ ID NO 24
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 24

Tyr Xaa Gln Gly Thr Phe Thr Ser Asp Tyr Ser Lys Tyr Leu Asp Glu
1               5                   10                  15

Cys Arg Ala Lys Glu Phe Val Gln Trp Leu Lys Asn Gly Gly Pro Ser
            20                  25                  30

Ser Gly Ala Pro Pro Pro Ser
        35

<210> SEQ ID NO 25
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)

<400> SEQUENCE: 25

His Xaa Gln Gly Thr Phe Thr Ser Asp Cys Ser Lys Tyr Leu Asp Glu
1               5                   10                  15

```
Arg Ala Ala Gln Asp Phe Val Gln Trp Leu Leu Asp Gly Gly Pro Ser
            20                  25                  30

Ser Gly Ala Pro Pro Pro Ser
        35


<210> SEQ ID NO 26
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)

<400> SEQUENCE: 26

His Xaa Gln Gly Thr Phe Thr Ser Asp Cys Ser Lys Tyr Leu Asp Ser
1               5                   10                  15

Arg Ala Ala Gln Asp Phe Val Gln Trp Leu Leu Asp Gly Gly Pro Ser
            20                  25                  30

Ser Gly Ala Pro Pro Pro Ser
        35


<210> SEQ ID NO 27
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)

<400> SEQUENCE: 27

His Xaa Gln Gly Thr Phe Thr Ser Asp Tyr Ser Lys Tyr Leu Asp Glu
1               5                   10                  15

Arg Ala Cys Gln Asp Phe Val Gln Trp Leu Leu Asp Gln Gly Gly Pro
            20                  25                  30

Ser Ser Gly Ala Pro Pro Pro Ser
        35                  40


<210> SEQ ID NO 28
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)

<400> SEQUENCE: 28

His Xaa Gln Gly Thr Phe Thr Ser Asp Tyr Ser Lys Tyr Leu Asp Glu
1               5                   10                  15

Lys Arg Ala Gln Glu Phe Val Cys Trp Leu Leu Ala Gln Lys Gly Lys
            20                  25                  30

Lys Asn Asp Trp Lys His Asn Ile Thr
        35                  40


<210> SEQ ID NO 29
<211> LENGTH: 30
```

<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 29

His Xaa Gln Gly Thr Phe Thr Ser Asp Tyr Ser Lys Tyr Leu Asp Glu
1 5 10 15

Lys Ala Ala Lys Glu Phe Val Gln Trp Leu Leu Asn Thr Cys
20 25 30

<210> SEQ ID NO 30
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 30

His Xaa Gln Gly Thr Phe Thr Ser Asp Tyr Ser Lys Tyr Leu Asp Glu
1 5 10 15

Lys Ala Gln Lys Glu Phe Val Gln Trp Leu Leu Asp Thr Cys
20 25 30

<210> SEQ ID NO 31
<211> LENGTH: 29
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 31

His Xaa Gln Gly Thr Phe Thr Ser Asp Tyr Ser Lys Tyr Leu Asp Glu
1 5 10 15

Lys Ala Cys Lys Glu Phe Val Gln Trp Leu Leu Ala Gln
20 25

<210> SEQ ID NO 32
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)

<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 32

His Xaa Gln Gly Thr Phe Thr Ser Asp Tyr Ser Lys Tyr Leu Asp Glu
1 5 10 15

Lys Ala Cys Lys Asp Phe Val Gln Trp Leu Leu Asp Gly Gly Pro Ser
20 25 30

Ser Gly Ala Pro Pro Pro Ser
35

<210> SEQ ID NO 33
<211> LENGTH: 31
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 33

His Xaa Gln Gly Thr Phe Thr Ser Asp Tyr Ser Ile Ala Met Asp Glu
1 5 10 15

Ile His Gln Lys Asp Phe Val Asn Trp Leu Leu Ala Gln Lys Cys
20 25 30

<210> SEQ ID NO 34
<211> LENGTH: 31
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 34

His Xaa Gln Gly Thr Phe Thr Ser Asp Tyr Ser Lys Tyr Leu Asp Glu
1 5 10 15

Lys Arg Gln Lys Glu Phe Val Asn Trp Leu Leu Ala Gln Lys Cys
20 25 30

<210> SEQ ID NO 35
<211> LENGTH: 31
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)

<223> OTHER INFORMATION: amino acids at positions 16 and 20 form a ring

<400> SEQUENCE: 35

His Xaa Gln Gly Thr Phe Thr Ser Asp Tyr Ser Ile Ala Met Asp Glu
1               5                   10                  15

Ile His Gln Lys Asp Phe Val Asn Trp Leu Leu Asn Thr Lys Cys
            20                  25                  30

<210> SEQ ID NO 36
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 36

His Xaa Gln Gly Thr Phe Thr Ser Asp Tyr Ser Lys Tyr Leu Cys Glu
1               5                   10                  15

Lys Arg Gln Lys Glu Phe Val Gln Trp Leu Leu Asn Gly Gly Pro Ser
            20                  25                  30

Ser Gly Ala Pro Pro Pro Ser Gly
        35                  40

<210> SEQ ID NO 37
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 37

His Xaa Gln Gly Thr Phe Thr Ser Asp Tyr Ser Lys Tyr Leu Asp Glu
1               5                   10                  15

Cys Arg Gln Lys Glu Phe Val Gln Trp Leu Leu Asn Gly Gly Pro Ser
            20                  25                  30

Ser Gly Ala Pro Pro Pro Ser Gly
        35                  40

<210> SEQ ID NO 38
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is 2-aminoisobutyric acid (Aib)

<400> SEQUENCE: 38

Xaa Xaa Gln Gly Thr Phe Thr Ser Asp Lys Ser Ser Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser Ser
        35                  40

<210> SEQ ID NO 39
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)

<400> SEQUENCE: 39

His Xaa Gln Gly Thr Phe Thr Ser Asp Tyr Ser Lys Tyr Leu Asp Gly
1               5                   10                  15

Gln His Ala Gln Cys Phe Val Ala Trp Leu Leu Ala Gly Gly Gly Pro
            20                  25                  30

Ser Ser Gly Ala Pro Pro Pro Ser
        35                  40

<210> SEQ ID NO 40
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)

<400> SEQUENCE: 40

His Xaa Gln Gly Thr Phe Thr Ser Asp Lys Ser Lys Tyr Leu Asp Glu
1               5                   10                  15

Arg Ala Cys Gln Asp Phe Val Gln Trp Leu Leu Asp Gly Gly Pro Ser
            20                  25                  30

Ser Gly Ala Pro Pro Pro Ser
        35

<210> SEQ ID NO 41
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)

<400> SEQUENCE: 41

His Xaa Gln Gly Thr Phe Thr Ser Asp Lys Ser Lys Tyr Leu Asp Glu
1               5                   10                  15

```
Cys Ala Ala Gln Asp Phe Val Gln Trp Leu Leu Asp Gly Gly Pro Ser
            20                  25                  30

Ser Gly Ala Pro Pro Pro Ser
        35


<210> SEQ ID NO 42
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 42

Tyr Xaa Gln Gly Thr Phe Thr Ser Asp Tyr Ser Lys Tyr Leu Asp Glu
1               5                   10                  15

Lys Arg Ala Lys Glu Phe Val Gln Trp Leu Leu Asp His His Pro Ser
            20                  25                  30

Ser Gly Gln Pro Pro Pro Ser Cys
        35                  40


<210> SEQ ID NO 43
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 43

Tyr Xaa Gln Gly Thr Phe Thr Ser Asp Tyr Ser Lys Tyr Leu Asp Glu
1               5                   10                  15

Lys Arg Ala Lys Glu Phe Val Gln Trp Leu Leu Asp His His Cys Ser
            20                  25                  30

Ser Gly Gln Pro Pro Pro Ser
        35


<210> SEQ ID NO 44
<211> LENGTH: 39
<212> TYPE: PRT
<213> ORGANISM: Artificial Sequence
<220> FEATURE:
<223> OTHER INFORMATION: Trigonal agonist

<400> SEQUENCE: 44

His Gly Gln Gly Thr Phe Thr Ser Asp Cys Ser Lys Gln Leu Asp Gly
1               5                   10                  15

Gln Ala Ala Gln Glu Phe Val Ala Trp Leu Leu Ala Gly Gly Pro Ser
            20                  25                  30

Ser Gly Ala Pro Pro Pro Ser
        35
```

<210> SEQ ID NO 45
<211> LENGTH: 39
<212> TYPE: PRT
<213> ORGANISM: Artificial Sequence
<220> FEATURE:
<223> OTHER INFORMATION: Trigonal agonist

<400> SEQUENCE: 45

His Gly Gln Gly Thr Phe Thr Ser Asp Cys Ser Lys Tyr Met Asp Gly
1 5 10 15

Gln Ala Ala Gln Asp Phe Val Ala Trp Leu Leu Ala Gly Gly Pro Ser
20 25 30

Ser Gly Ala Pro Pro Pro Ser
35

<210> SEQ ID NO 46
<211> LENGTH: 39
<212> TYPE: PRT
<213> ORGANISM: Artificial Sequence
<220> FEATURE:
<223> OTHER INFORMATION: Trigonal agonist

<400> SEQUENCE: 46

His Gly Gln Gly Thr Phe Thr Ser Asp Cys Ser Lys Tyr Leu Asp Glu
1 5 10 15

Gln His Ala Gln Glu Phe Val Ala Trp Leu Leu Ala Gly Gly Pro Ser
20 25 30

Ser Gly Ala Pro Pro Pro Ser
35

<210> SEQ ID NO 47
<211> LENGTH: 39
<212> TYPE: PRT
<213> ORGANISM: Artificial Sequence
<220> FEATURE:
<223> OTHER INFORMATION: Trigonal agonist

<400> SEQUENCE: 47

His Gly Gln Gly Thr Phe Thr Ser Asp Cys Ser Lys Tyr Leu Asp Gly
1 5 10 15

Gln Arg Ala Gln Glu Phe Val Ala Trp Leu Leu Ala Gly Gly Pro Ser
20 25 30

Ser Gly Ala Pro Pro Pro Ser
35

<210> SEQ ID NO 48
<211> LENGTH: 39
<212> TYPE: PRT
<213> ORGANISM: Artificial Sequence
<220> FEATURE:
<223> OTHER INFORMATION: Trigonal agonist

<400> SEQUENCE: 48

His Gly Gln Gly Thr Phe Thr Ser Asp Cys Ser Lys Tyr Leu Asp Gly
1 5 10 15

Gln Arg Ala Gln Asp Phe Val Asn Trp Leu Leu Ala Gly Gly Pro Ser
20 25 30

Ser Gly Ala Pro Pro Pro Ser
35

<210> SEQ ID NO 49

<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 49

```
Xaa Xaa Gln Gly Thr Phe Thr Ser Asp Tyr Ser Ile Cys Met Asp Glu
1               5                   10                  15

Ile His Gln Lys Asp Phe Val Asn Trp Leu Leu Asn Thr Lys
            20                  25                  30
```

<210> SEQ ID NO 50
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 50

```
His Xaa Gln Gly Thr Phe Thr Ser Asp Tyr Ser Lys Tyr Leu Asp Glu
1               5                   10                  15

Lys Arg Ala Lys Glu Phe Val Gln Trp Leu Leu Asp His His Pro Ser
            20                  25                  30

Ser Gly Gln Pro Pro Pro Ser Cys
        35                  40
```

<210> SEQ ID NO 51
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 51

```
His Xaa Gln Gly Thr Phe Thr Ser Asp Tyr Ser Lys Tyr Leu Asp Glu
1               5                   10                  15

Lys Arg Gln Lys Glu Phe Val Gln Trp Leu Leu Asn Thr Cys
            20                  25                  30
```

<210> SEQ ID NO 52

<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 52

```
His Xaa Gln Gly Thr Phe Thr Ser Asp Tyr Ser Lys Tyr Leu Asp Glu
1               5                   10                  15

Lys Arg Gln Lys Glu Phe Val Gln Trp Leu Leu Asp Thr Cys
            20                  25                  30
```

<210> SEQ ID NO 53
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 53

```
His Xaa Glu Gly Thr Phe Thr Ser Asp Tyr Ser Ile Ala Met Asp Glu
1               5                   10                  15

Ile His Gln Lys Asp Phe Val Asn Trp Leu Leu Ala Gln Cys
            20                  25                  30
```

<210> SEQ ID NO 54
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 54

```
His Xaa Glu Gly Thr Phe Thr Ser Asp Tyr Ser Ile Ala Met Asp Glu
1               5                   10                  15

Ile His Gln Lys Asp Phe Val Asp Trp Leu Leu Ala Glu Cys
            20                  25                  30
```

<210> SEQ ID NO 55
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 55

```
His Xaa Gln Gly Thr Phe Thr Ser Asp Tyr Ser Ile Ala Met Asp Glu
1               5                   10                  15

Ile His Gln Lys Asp Phe Val Asn Trp Leu Leu Ala Gln Cys
            20                  25                  30
```

<210> SEQ ID NO 56
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 56

```
His Xaa Gln Gly Thr Phe Thr Ser Asp Tyr Ser Lys Tyr Leu Asp Glu
1               5                   10                  15

Lys Arg Gln Lys Glu Phe Val Asn Trp Leu Leu Ala Gln Cys
            20                  25                  30
```

<210> SEQ ID NO 57
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 57

```
His Xaa Gln Gly Thr Phe Thr Ser Asp Tyr Ser Ile Ala Met Asp Glu
1               5                   10                  15

Ile His Gln Lys Asp Phe Val Asn Trp Leu Leu Asn Thr Cys
            20                  25                  30
```

<210> SEQ ID NO 58
<211> LENGTH: 31
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 58

His Xaa Gln Gly Thr Phe Thr Ser Asp Tyr Ser Lys Tyr Leu Asp Glu
1 5 10 15

Lys Arg Gln Lys Glu Phe Val Gln Trp Leu Leu Asn Thr Lys Cys
20 25 30

<210> SEQ ID NO 59
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 59

Xaa Xaa Gln Gly Thr Phe Thr Ser Asp Tyr Ser Ile Cys Met Asp Glu
1 5 10 15

Lys His Gln Lys Asp Phe Val Asn Trp Leu Leu Asn Thr Lys
20 25 30

<210> SEQ ID NO 60
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 60

Xaa Xaa Gln Gly Thr Phe Thr Ser Asp Tyr Ser Ile Ala Met Asp Glu
1 5 10 15

Lys His Cys Lys Asp Phe Val Asn Trp Leu Leu Asn Thr Lys
20 25 30

<210> SEQ ID NO 61
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is 2-aminoisobutyric acid (Aib)

<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 61

```
Xaa Xaa Gln Gly Thr Phe Thr Ser Asp Tyr Ser Ile Ala Met Asp Glu
1               5                   10                  15

Ile Ala Cys Lys Asp Phe Val Asn Trp Leu Leu Asn Thr Lys
            20                  25                  30
```

<210> SEQ ID NO 62
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is 2-aminoisobutyric acid (Aib)

<400> SEQUENCE: 62

```
Xaa Xaa Gln Gly Thr Phe Thr Ser Asp Lys Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser
        35
```

<210> SEQ ID NO 63
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is 2-aminoisobutyric acid (Aib)

<400> SEQUENCE: 63

```
Xaa Xaa Gln Gly Thr Phe Thr Ser Asp Cys Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser
        35
```

<210> SEQ ID NO 64
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:

<221> NAME/KEY: MISC_FEATURE
<222> LOCATION: (16)..(20)
<223> OTHER INFORMATION: amino acids at positions 16 and 20 form a ring

<400> SEQUENCE: 64

```
Tyr Xaa Gln Gly Thr Phe Thr Ser Asp Tyr Ser Lys Tyr Leu Asp Glu
1               5                   10                  15

Cys Ala Ala Lys Glu Phe Val Gln Trp Leu Leu Asp His His Pro Ser
            20                  25                  30

Ser Gly Gln Pro Pro Pro Ser
        35
```

<210> SEQ ID NO 65
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 65

```
His Xaa Gln Gly Thr Phe Thr Ser Asp Tyr Ser Lys Cys Leu Asp Glu
1               5                   10                  15

Lys Arg Ala Lys Glu Phe Val Gln Trp Leu Leu Asp His His Pro Ser
            20                  25                  30

Ser Gly Gln Pro Pro Pro Ser
        35
```

<210> SEQ ID NO 66
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 66

```
Tyr Xaa Gln Gly Thr Phe Thr Ser Asp Tyr Ser Lys Tyr Leu Asp Glu
1               5                   10                  15

Cys Arg Ala Lys Asp Phe Val Gln Trp Leu Leu Asp His His Pro Ser
            20                  25                  30

Ser Gly Gln Pro Pro Pro Ser
        35
```

<210> SEQ ID NO 67
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)

<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 67

Tyr Xaa Gln Gly Thr Phe Thr Ser Asp Tyr Ser Lys Tyr Leu Asp Glu
1               5                   10                  15

Cys Ala Ala Lys Asp Phe Val Gln Trp Leu Leu Asp His His Pro Ser
            20                  25                  30

Ser Gly Gln Pro Pro Pro Ser
        35

<210> SEQ ID NO 68
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 68

Tyr Xaa Gln Gly Thr Phe Thr Ser Asp Tyr Ser Lys Cys Leu Asp Glu
1               5                   10                  15

Lys Ala Ala Lys Glu Phe Val Gln Trp Leu Leu Asp His His Pro Ser
            20                  25                  30

Ser Gly Gln Pro Pro Pro Ser
        35

<210> SEQ ID NO 69
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 69

Tyr Xaa Gln Gly Thr Phe Thr Ser Asp Tyr Ser Lys Cys Leu Asp Glu
1               5                   10                  15

Arg Ala Ala Lys Glu Phe Val Gln Trp Leu Leu Asp His His Pro Ser
            20                  25                  30

Ser Gly Gln Pro Pro Pro Ser
        35

<210> SEQ ID NO 70
<211> LENGTH: 39
<212> TYPE: PRT
<213> ORGANISM: Artificial Sequence
<220> FEATURE:
<223> OTHER INFORMATION: Trigonal agonist
<220> FEATURE:

<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 70

```
Tyr Xaa Gln Gly Thr Phe Thr Ser Asp Tyr Ser Lys Cys Leu Asp Glu
1               5                   10                  15

Lys Arg Ala Lys Asp Phe Val Gln Trp Leu Leu Asp His His Pro Ser
            20                  25                  30

Ser Gly Gln Pro Pro Pro Ser
        35
```

<210> SEQ ID NO 71
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 71

```
Tyr Xaa Gln Gly Thr Phe Thr Ser Asp Tyr Ser Lys Tyr Leu Asp Glu
1               5                   10                  15

Arg Ala Cys Lys Asp Phe Val Gln Trp Leu Leu Asp His His Pro Ser
            20                  25                  30

Ser Gly Gln Pro Pro Pro Ser
        35
```

<210> SEQ ID NO 72
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 72

```
Tyr Xaa Gln Gly Thr Phe Thr Ser Asp Cys Ser Lys Tyr Leu Asp Glu
1               5                   10                  15

Arg Ala Ala Lys Asp Phe Val Gln Trp Leu Leu Asp His His Pro Ser
            20                  25                  30

Ser Gly Gln Pro Pro Pro Ser
        35
```

<210> SEQ ID NO 73
<211> LENGTH: 39
<212> TYPE: PRT
<213> ORGANISM: Artificial Sequence
<220> FEATURE:

<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 73

```
Xaa Xaa Gln Gly Thr Phe Thr Ser Asp Tyr Ser Lys Tyr Leu Asp Glu
1               5                   10                  15

Cys Arg Ala Lys Glu Phe Val Gln Trp Leu Leu Asp His His Pro Ser
            20                  25                  30

Ser Gly Gln Pro Pro Pro Ser
        35
```

<210> SEQ ID NO 74
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 74

```
Xaa Xaa Gln Gly Thr Phe Thr Ser Asp Tyr Ser Lys Cys Leu Asp Glu
1               5                   10                  15

Lys Arg Ala Lys Glu Phe Val Gln Trp Leu Leu Asp His His Pro Ser
            20                  25                  30

Ser Gly Gln Pro Pro Pro Ser
        35
```

<210> SEQ ID NO 75
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 75

```
Tyr Xaa Gln Gly Thr Phe Thr Ser Asp Tyr Ser Lys Tyr Leu Asp Glu
1               5                   10                  15

Lys Ala Ala Lys Glu Phe Val Gln Trp Leu Leu Asp His His Pro Ser
            20                  25                  30
```

```
Ser Gly Gln Pro Pro Pro Ser Cys
        35                  40


<210> SEQ ID NO 76
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 76

Tyr Xaa Gln Gly Thr Phe Thr Ser Asp Tyr Ser Lys Tyr Leu Asp Glu
1               5                   10                  15

Lys Arg Ala Lys Asp Phe Val Gln Trp Leu Leu Asp His His Pro Ser
            20                  25                  30

Ser Gly Gln Pro Pro Pro Ser Cys
        35                  40


<210> SEQ ID NO 77
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 77

Tyr Xaa Gln Gly Thr Phe Thr Ser Asp Tyr Ser Lys Tyr Leu Asp Glu
1               5                   10                  15

Lys Ala Ala Lys Asp Phe Val Gln Trp Leu Leu Asp His His Pro Ser
            20                  25                  30

Ser Gly Gln Pro Pro Pro Ser Cys
        35                  40


<210> SEQ ID NO 78
<211> LENGTH: 31
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 78

His Xaa Gln Gly Thr Phe Thr Ser Asp Tyr Ser Lys Tyr Leu Asp Glu
1               5                   10                  15
```

Lys Arg Gln Lys Glu Phe Val Gln Trp Leu Leu Asp Thr Lys Cys
20 25 30

<210> SEQ ID NO 79
<211> LENGTH: 31
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 79

His Xaa Glu Gly Thr Phe Thr Ser Asp Tyr Ser Ile Ala Met Asp Glu
1 5 10 15

Ile His Gln Lys Asp Phe Val Asn Trp Leu Leu Ala Gln Lys Cys
20 25 30

<210> SEQ ID NO 80
<211> LENGTH: 31
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 80

His Xaa Glu Gly Thr Phe Thr Ser Asp Tyr Ser Ile Ala Met Asp Glu
1 5 10 15

Ile His Gln Lys Asp Phe Val Asp Trp Leu Leu Ala Glu Lys Cys
20 25 30

<210> SEQ ID NO 81
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 81

Xaa Xaa Gln Gly Thr Phe Thr Ser Asp Tyr Ser Lys Tyr Leu Asp Glu
1 5 10 15

Lys Arg Gln Lys Glu Phe Val Gln Trp Leu Leu Asn Thr Cys
20 25 30

<210> SEQ ID NO 82
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 82

```
Xaa Xaa Gln Gly Thr Phe Thr Ser Asp Tyr Ser Lys Tyr Leu Asp Glu
1               5                   10                  15

Lys Arg Gln Lys Glu Phe Val Gln Trp Leu Leu Asp Thr Cys
            20                  25                  30
```

<210> SEQ ID NO 83
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 83

```
Xaa Xaa Glu Gly Thr Phe Thr Ser Asp Tyr Ser Ile Ala Met Asp Glu
1               5                   10                  15

Ile His Gln Lys Asp Phe Val Asn Trp Leu Leu Ala Gln Cys
            20                  25                  30
```

<210> SEQ ID NO 84
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 84

```
Xaa Xaa Glu Gly Thr Phe Thr Ser Asp Tyr Ser Ile Ala Met Asp Glu
1               5                   10                  15

Ile His Gln Lys Asp Phe Val Asp Trp Leu Leu Ala Glu Cys
            20                  25                  30
```

<210> SEQ ID NO 85
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 85

```
Xaa Xaa Gln Gly Thr Phe Thr Ser Asp Tyr Ser Ile Ala Met Asp Glu
1               5                   10                  15

Ile His Gln Lys Asp Phe Val Asn Trp Leu Leu Ala Gln Cys
            20                  25                  30
```

<210> SEQ ID NO 86
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 86

```
Xaa Xaa Gln Gly Thr Phe Thr Ser Asp Tyr Ser Lys Tyr Leu Asp Glu
1               5                   10                  15

Lys Arg Gln Lys Glu Phe Val Asn Trp Leu Leu Ala Gln Cys
            20                  25                  30
```

<210> SEQ ID NO 87
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)

```
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 87

Xaa Xaa Gln Gly Thr Phe Thr Ser Asp Tyr Ser Ile Ala Met Asp Glu
1               5                   10                  15

Ile His Gln Lys Asp Phe Val Asn Trp Leu Leu Asn Thr Cys
            20                  25                  30


<210> SEQ ID NO 88
<211> LENGTH: 31
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 88

Xaa Xaa Gln Gly Thr Phe Thr Ser Asp Tyr Ser Lys Tyr Leu Asp Glu
1               5                   10                  15

Lys Arg Gln Lys Glu Phe Val Gln Trp Leu Leu Asn Thr Lys Cys
            20                  25                  30


<210> SEQ ID NO 89
<211> LENGTH: 31
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 89

Xaa Xaa Gln Gly Thr Phe Thr Ser Asp Tyr Ser Lys Tyr Leu Asp Glu
1               5                   10                  15

Lys Arg Gln Lys Glu Phe Val Gln Trp Leu Leu Asp Thr Lys Cys
            20                  25                  30


<210> SEQ ID NO 90
<211> LENGTH: 31
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
```

<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 90

```
Xaa Xaa Glu Gly Thr Phe Thr Ser Asp Tyr Ser Ile Ala Met Asp Glu
1               5                   10                  15

Ile His Gln Lys Asp Phe Val Asn Trp Leu Leu Ala Gln Lys Cys
            20                  25                  30
```

<210> SEQ ID NO 91
<211> LENGTH: 31
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 91

```
Xaa Xaa Glu Gly Thr Phe Thr Ser Asp Tyr Ser Ile Ala Met Asp Glu
1               5                   10                  15

Ile His Gln Lys Asp Phe Val Asp Trp Leu Leu Ala Glu Lys Cys
            20                  25                  30
```

<210> SEQ ID NO 92
<211> LENGTH: 31
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 92

```
Xaa Xaa Gln Gly Thr Phe Thr Ser Asp Tyr Ser Ile Ala Met Asp Glu
1               5                   10                  15

Ile His Gln Lys Asp Phe Val Asn Trp Leu Leu Ala Gln Lys Cys
            20                  25                  30
```

<210> SEQ ID NO 93
<211> LENGTH: 31
<212> TYPE: PRT

```
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 93

Xaa Xaa Gln Gly Thr Phe Thr Ser Asp Tyr Ser Lys Tyr Leu Asp Glu
1               5                   10                  15

Lys Arg Gln Lys Glu Phe Val Asn Trp Leu Leu Ala Gln Lys Cys
            20                  25                  30


<210> SEQ ID NO 94
<211> LENGTH: 31
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 94

Xaa Xaa Gln Gly Thr Phe Thr Ser Asp Tyr Ser Ile Ala Met Asp Glu
1               5                   10                  15

Ile His Gln Lys Asp Phe Val Asn Trp Leu Leu Asn Thr Lys Cys
            20                  25                  30


<210> SEQ ID NO 95
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 95

Tyr Xaa Gln Gly Thr Phe Thr Ser Asp Tyr Ser Lys Tyr Leu Asp Glu
1               5                   10                  15

Lys Arg Ala Lys Glu Phe Val Gln Trp Leu Leu Cys His His Pro Ser
            20                  25                  30

Ser Gly Gln Pro Pro Pro Ser
        35
```

<210> SEQ ID NO 96
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 96

```
Tyr Xaa Gln Gly Thr Phe Thr Ser Asp Tyr Ser Lys Tyr Leu Asp Glu
1               5                   10                  15

Lys Arg Ala Lys Glu Phe Val Gln Trp Leu Leu Asp His Cys Pro Ser
            20                  25                  30

Ser Gly Gln Pro Pro Pro Ser
        35
```

<210> SEQ ID NO 97
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 97

```
Tyr Xaa Gln Gly Thr Phe Thr Ser Asp Tyr Ser Lys Tyr Leu Asp Glu
1               5                   10                  15

Lys Arg Ala Lys Glu Phe Val Gln Trp Leu Leu Asp Cys His Pro Ser
            20                  25                  30

Ser Gly Gln Pro Pro Pro Ser
        35
```

<210> SEQ ID NO 98
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 98

```
Tyr Xaa Gln Gly Thr Phe Thr Ser Asp Tyr Ser Lys Ala Leu Asp Glu
1               5                   10                  15
```

Lys Ala Ala Lys Glu Phe Val Asn Trp Leu Leu Asp His His Pro Ser
20 25 30

Ser Gly Gln Pro Pro Pro Ser Cys
35 40

<210> SEQ ID NO 99
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 99

Tyr Xaa Gln Gly Thr Phe Thr Ser Asp Tyr Ser Lys Ala Leu Asp Glu
1 5 10 15

Lys Ala Ala Lys Asp Phe Val Asn Trp Leu Leu Asp His His Pro Ser
20 25 30

Ser Gly Gln Pro Pro Pro Ser Cys
35 40

<210> SEQ ID NO 100
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 100

Tyr Xaa Gln Gly Thr Phe Thr Ser Asp Tyr Ser Lys Ala Leu Asp Glu
1 5 10 15

Lys Ala Ala Lys Glu Phe Val Gln Trp Leu Leu Asp Gln His Pro Ser
20 25 30

Ser Gly Gln Pro Pro Pro Ser Cys
35 40

<210> SEQ ID NO 101
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 101

Tyr Xaa Gln Gly Thr Phe Thr Ser Asp Tyr Ser Lys Ala Leu Asp Glu
1 5 10 15

Lys Ala Ala Lys Glu Phe Val Asn Trp Leu Leu Asp Gln His Pro Ser
20 25 30

Ser Gly Gln Pro Pro Pro Ser Cys
35 40

<210> SEQ ID NO 102
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is 2-aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 102

Tyr Xaa Gln Gly Thr Phe Thr Ser Asp Tyr Ser Lys Ala Leu Asp Glu
1 5 10 15

Lys Ala Ala Lys Asp Phe Val Asn Trp Leu Leu Asp Gln His Pro Ser
20 25 30

Ser Gly Gln Pro Pro Pro Ser Cys
35 40

<210> SEQ ID NO 103
<211> LENGTH: 12
<212> TYPE: PRT
<213> ORGANISM: HOMO SAPIENS

<400> SEQUENCE: 103

Glu Ser Lys Tyr Gly Pro Pro Cys Pro Ser Cys Pro
1 5 10

<210> SEQ ID NO 104
<211> LENGTH: 11
<212> TYPE: PRT
<213> ORGANISM: Artificial Sequence
<220> FEATURE:
<223> OTHER INFORMATION: Variant of hinge region

<400> SEQUENCE: 104

Glu Ser Lys Tyr Gly Pro Pro Pro Ser Cys Pro
1 5 10

<210> SEQ ID NO 105
<211> LENGTH: 11
<212> TYPE: PRT
<213> ORGANISM: Artificial Sequence
<220> FEATURE:
<223> OTHER INFORMATION: Variant of hinge region

<400> SEQUENCE: 105

Glu Ser Lys Tyr Gly Pro Pro Cys Pro Ser Pro
1 5 10

<210> SEQ ID NO 106
<211> LENGTH: 10

<212> TYPE: PRT
<213> ORGANISM: Artificial Sequence
<220> FEATURE:
<223> OTHER INFORMATION: Variant of hinge region

<400> SEQUENCE: 106

Glu Ser Lys Tyr Gly Pro Pro Cys Pro Ser
1 5 10

<210> SEQ ID NO 107
<211> LENGTH: 10
<212> TYPE: PRT
<213> ORGANISM: Artificial Sequence
<220> FEATURE:
<223> OTHER INFORMATION: Variant of hinge region

<400> SEQUENCE: 107

Glu Ser Lys Tyr Gly Pro Pro Cys Pro Pro
1 5 10

<210> SEQ ID NO 108
<211> LENGTH: 8
<212> TYPE: PRT
<213> ORGANISM: Artificial Sequence
<220> FEATURE:
<223> OTHER INFORMATION: Variant of hinge region

<400> SEQUENCE: 108

Lys Tyr Gly Pro Pro Cys Pro Ser
1 5

<210> SEQ ID NO 109
<211> LENGTH: 8
<212> TYPE: PRT
<213> ORGANISM: Artificial Sequence
<220> FEATURE:
<223> OTHER INFORMATION: Variant of hinge region

<400> SEQUENCE: 109

Glu Ser Lys Tyr Gly Pro Pro Cys
1 5

<210> SEQ ID NO 110
<211> LENGTH: 7
<212> TYPE: PRT
<213> ORGANISM: Artificial Sequence
<220> FEATURE:
<223> OTHER INFORMATION: Variant of hinge region

<400> SEQUENCE: 110

Glu Lys Tyr Gly Pro Pro Cys
1 5

<210> SEQ ID NO 111
<211> LENGTH: 6
<212> TYPE: PRT
<213> ORGANISM: Artificial Sequence
<220> FEATURE:
<223> OTHER INFORMATION: Variant of hinge region

<400> SEQUENCE: 111

Glu Ser Pro Ser Cys Pro
1 5

<210> SEQ ID NO 112
<211> LENGTH: 5
<212> TYPE: PRT

<213> ORGANISM: Artificial Sequence
<220> FEATURE:
<223> OTHER INFORMATION: Variant of hinge region

<400> SEQUENCE: 112

Glu Pro Ser Cys Pro
1               5

<210> SEQ ID NO 113
<211> LENGTH: 4
<212> TYPE: PRT
<213> ORGANISM: Artificial Sequence
<220> FEATURE:
<223> OTHER INFORMATION: Variant of hinge region

<400> SEQUENCE: 113

Pro Ser Cys Pro
1

<210> SEQ ID NO 114
<211> LENGTH: 10
<212> TYPE: PRT
<213> ORGANISM: Artificial Sequence
<220> FEATURE:
<223> OTHER INFORMATION: Variant of hinge region

<400> SEQUENCE: 114

Glu Ser Lys Tyr Gly Pro Pro Ser Cys Pro
1               5                   10

<210> SEQ ID NO 115
<211> LENGTH: 9
<212> TYPE: PRT
<213> ORGANISM: Artificial Sequence
<220> FEATURE:
<223> OTHER INFORMATION: Variant of hinge region

<400> SEQUENCE: 115

Lys Tyr Gly Pro Pro Pro Ser Cys Pro
1               5

<210> SEQ ID NO 116
<211> LENGTH: 9
<212> TYPE: PRT
<213> ORGANISM: Artificial Sequence
<220> FEATURE:
<223> OTHER INFORMATION: Variant of hinge region

<400> SEQUENCE: 116

Glu Ser Lys Tyr Gly Pro Ser Cys Pro
1               5

<210> SEQ ID NO 117
<211> LENGTH: 8
<212> TYPE: PRT
<213> ORGANISM: Artificial Sequence
<220> FEATURE:
<223> OTHER INFORMATION: Variant of hinge region

<400> SEQUENCE: 117

Glu Ser Lys Tyr Gly Pro Pro Cys
1               5

<210> SEQ ID NO 118
<211> LENGTH: 7
<212> TYPE: PRT
<213> ORGANISM: Artificial Sequence
<220> FEATURE:
<223> OTHER INFORMATION: Variant of hinge region

<400> SEQUENCE: 118

Lys Tyr Gly Pro Pro Cys Pro
1 5

<210> SEQ ID NO 119
<211> LENGTH: 7
<212> TYPE: PRT
<213> ORGANISM: Artificial Sequence
<220> FEATURE:
<223> OTHER INFORMATION: Variant of hinge region

<400> SEQUENCE: 119

Glu Ser Lys Pro Ser Cys Pro
1 5

<210> SEQ ID NO 120
<211> LENGTH: 6
<212> TYPE: PRT
<213> ORGANISM: Artificial Sequence
<220> FEATURE:
<223> OTHER INFORMATION: Variant of hinge region

<400> SEQUENCE: 120

Glu Ser Pro Ser Cys Pro
1 5

<210> SEQ ID NO 121
<211> LENGTH: 4
<212> TYPE: PRT
<213> ORGANISM: Artificial Sequence
<220> FEATURE:
<223> OTHER INFORMATION: Variant of hinge region

<400> SEQUENCE: 121

Glu Pro Ser Cys
1

<210> SEQ ID NO 122
<211> LENGTH: 3
<212> TYPE: PRT
<213> ORGANISM: Artificial Sequence
<220> FEATURE:
<223> OTHER INFORMATION: Variant of hinge region

<400> SEQUENCE: 122

Ser Cys Pro
1

<210> SEQ ID NO 123
<211> LENGTH: 221
<212> TYPE: PRT
<213> ORGANISM: homo sapiens

<400> SEQUENCE: 123

Pro Ser Cys Pro Ala Pro Glu Phe Leu Gly Gly Pro Ser Val Phe Leu
1 5 10 15

Phe Pro Pro Lys Pro Lys Asp Thr Leu Met Ile Ser Arg Thr Pro Glu
20 25 30

Val Thr Cys Val Val Val Asp Val Ser Gln Glu Asp Pro Glu Val Gln
35 40 45

Phe Asn Trp Tyr Val Asp Gly Val Glu Val His Asn Ala Lys Thr Lys
50 55 60

```
Pro Arg Glu Glu Gln Phe Asn Ser Thr Tyr Arg Val Val Ser Val Leu
65                  70                  75                  80

Thr Val Leu His Gln Asp Trp Leu Asn Gly Lys Glu Tyr Lys Cys Lys
                85                  90                  95

Val Ser Asn Lys Gly Leu Pro Ser Ser Ile Glu Lys Thr Ile Ser Lys
            100                 105                 110

Ala Lys Gly Gln Pro Arg Glu Pro Gln Val Tyr Thr Leu Pro Pro Ser
        115                 120                 125

Gln Glu Glu Met Thr Lys Asn Gln Val Ser Leu Thr Cys Leu Val Lys
    130                 135                 140

Gly Phe Tyr Pro Ser Asp Ile Ala Val Glu Trp Glu Ser Asn Gly Gln
145                 150                 155                 160

Pro Glu Asn Asn Tyr Lys Thr Thr Pro Pro Val Leu Asp Ser Asp Gly
                165                 170                 175

Ser Phe Phe Leu Tyr Ser Arg Leu Thr Val Asp Lys Ser Arg Trp Gln
            180                 185                 190

Glu Gly Asn Val Phe Ser Cys Ser Val Met His Glu Ala Leu His Asn
        195                 200                 205

His Tyr Thr Gln Lys Ser Leu Ser Leu Ser Leu Gly Lys
    210                 215                 220
```

<210> SEQ ID NO 124
<211> LENGTH: 21
<212> TYPE: DNA
<213> ORGANISM: Artificial Sequence
<220> FEATURE:
<223> OTHER INFORMATION: Forward primer of RUNX2

<400> SEQUENCE: 124
gccctcatcc ttcactccaa g 21

<210> SEQ ID NO 125
<211> LENGTH: 21
<212> TYPE: DNA
<213> ORGANISM: Artificial Sequence
<220> FEATURE:
<223> OTHER INFORMATION: Reverse primer of RUNX2

<400> SEQUENCE: 125
ggtcagtcag tgcctttcct c 21

<210> SEQ ID NO 126
<211> LENGTH: 20
<212> TYPE: DNA
<213> ORGANISM: Artificial Sequence
<220> FEATURE:
<223> OTHER INFORMATION: Forward primer of OCN

<400> SEQUENCE: 126
gagggcaata aggtagtgaa 20

<210> SEQ ID NO 127
<211> LENGTH: 19
<212> TYPE: DNA
<213> ORGANISM: Artificial Sequence
<220> FEATURE:
<223> OTHER INFORMATION: Reverse primer of OCN

<400> SEQUENCE: 127
catagatgcg tttgtaggc 19

<210> SEQ ID NO 128
<211> LENGTH: 20
<212> TYPE: DNA
<213> ORGANISM: Artificial Sequence
<220> FEATURE:
<223> OTHER INFORMATION: Forward primer of ALP

<400> SEQUENCE: 128
ccagcaggtt tctctcttgg 20

<210> SEQ ID NO 129
<211> LENGTH: 20
<212> TYPE: DNA
<213> ORGANISM: Artificial Sequence
<220> FEATURE:
<223> OTHER INFORMATION: Reverse primer of ALP

<400> SEQUENCE: 129
ggaatgttcc atggaggttg 20

<210> SEQ ID NO 130
<211> LENGTH: 20
<212> TYPE: DNA
<213> ORGANISM: Artificial Sequence
<220> FEATURE:
<223> OTHER INFORMATION: Forward primer of ColA1

<400> SEQUENCE: 130
agagcatgac cgatggattc 20

<210> SEQ ID NO 131
<211> LENGTH: 20
<212> TYPE: DNA
<213> ORGANISM: Artificial Sequence
<220> FEATURE:
<223> OTHER INFORMATION: Reverse primer of ColA1

<400> SEQUENCE: 131
ccttcttgag gttgccagtc 20

<210> SEQ ID NO 132
<211> LENGTH: 19
<212> TYPE: DNA
<213> ORGANISM: Artificial Sequence
<220> FEATURE:
<223> OTHER INFORMATION: Forward primer of GAPDH

<400> SEQUENCE: 132
gtcgtggatc tgacgtgcc 19

<210> SEQ ID NO 133
<211> LENGTH: 19
<212> TYPE: DNA
<213> ORGANISM: Artificial Sequence
<220> FEATURE:
<223> OTHER INFORMATION: Reverse primer of GAPDH

<400> SEQUENCE: 133
tgcctgcttc accaccttc 19

<210> SEQ ID NO 134
<211> LENGTH: 442
<212> TYPE: PRT
<213> ORGANISM: Homo sapiens
<220> FEATURE:
<221> NAME/KEY: MISC_FEATURE
<222> LOCATION: (1)..(442)
<223> OTHER INFORMATION: Amino acids at position 1 to 442 form Human Immunoglobulin G4 Fc Fragment (homodimer)
<220> FEATURE:
<221> NAME/KEY: MISC_FEATURE
<222> LOCATION: (1)..(221)
<223> OTHER INFORMATION: Amino acids at position 1 to 221 form one monomer
<220> FEATURE:
<221> NAME/KEY: MISC_FEATURE
<222> LOCATION: (222)..(442)
<223> OTHER INFORMATION: Amino acids at position 222 to 442 form one monomer
<220> FEATURE:
<221> NAME/KEY: DISULFID
<222> LOCATION: (3)..(224)
<223> OTHER INFORMATION: Amino acids at position 3 and position 224 form an inter-disulfide bond
<220> FEATURE:
<221> NAME/KEY: DISULFID
<222> LOCATION: (35)..(95)
<223> OTHER INFORMATION: Amino acids at position 35 and position 95 form an intra-chain disulfide bond
<220> FEATURE:
<221> NAME/KEY: DISULFID
<222> LOCATION: (141)..(199)
<223> OTHER INFORMATION: Amino acids at position 141 and position 199 form an intra-chain disulfide bond
<220> FEATURE:
<221> NAME/KEY: DISULFID
<222> LOCATION: (256)..(316)
<223> OTHER INFORMATION: Amino acids at position 256 and position 316 form an intra-chain disulfide bond
<220> FEATURE:
<221> NAME/KEY: DISULFID
<222> LOCATION: (362)..(420)
<223> OTHER INFORMATION: Amino acids at position 362 and position 420 form an intra-chain disulfide bond

<400> SEQUENCE: 134

```
Pro Ser Cys Pro Ala Pro Glu Phe Leu Gly Gly Pro Ser Val Phe Leu
1               5                   10                  15

Phe Pro Pro Lys Pro Lys Asp Thr Leu Met Ile Ser Arg Thr Pro Glu
            20                  25                  30

Val Thr Cys Val Val Val Asp Val Ser Gln Glu Asp Pro Glu Val Gln
        35                  40                  45

Phe Asn Trp Tyr Val Asp Gly Val Glu Val His Asn Ala Lys Thr Lys
    50                  55                  60

Pro Arg Glu Glu Gln Phe Asn Ser Thr Tyr Arg Val Val Ser Val Leu
65                  70                  75                  80

Thr Val Leu His Gln Asp Trp Leu Asn Gly Lys Glu Tyr Lys Cys Lys
                85                  90                  95

Val Ser Asn Lys Gly Leu Pro Ser Ser Ile Glu Lys Thr Ile Ser Lys
            100                 105                 110

Ala Lys Gly Gln Pro Arg Glu Pro Gln Val Tyr Thr Leu Pro Pro Ser
        115                 120                 125

Gln Glu Glu Met Thr Lys Asn Gln Val Ser Leu Thr Cys Leu Val Lys
    130                 135                 140

Gly Phe Tyr Pro Ser Asp Ile Ala Val Glu Trp Glu Ser Asn Gly Gln
145                 150                 155                 160

Pro Glu Asn Asn Tyr Lys Thr Thr Pro Pro Val Leu Asp Ser Asp Gly
                165                 170                 175

Ser Phe Phe Leu Tyr Ser Arg Leu Thr Val Asp Lys Ser Arg Trp Gln
            180                 185                 190

Glu Gly Asn Val Phe Ser Cys Ser Val Met His Glu Ala Leu His Asn
        195                 200                 205
```

-continued

```
His Tyr Thr Gln Lys Ser Leu Ser Leu Ser Leu Gly Lys Pro Ser Cys
    210                 215                 220

Pro Ala Pro Glu Phe Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
            420                 425                 430

Gln Lys Ser Leu Ser Leu Ser Leu Gly Lys
        435                 440
```

PHARMACEUTICAL COMPOSITION FOR PREVENTING OR TREATING BONE DISEASES, COMPRISING TRIPLE AGONIST OR CONJUGATE THEREOF HAVING ACTIVITY WITH RESPECT TO ALL OF GLUCAGON, GLP-1 AND GLP RECEPTORS

CROSS REFERENCE TO RELATED APPLICATIONS

This application is a National Stage of International Application No. PCT/KR2021/013007 filed Sep. 24, 2021, claiming priority based on Korean Patent Application No. 10-2020-0125196 filed Sep. 25, 2020.

INCORPORATION BY REFERENCE OF SEQUENCE LISTING

The content of the electronically submitted sequence listing, file name: Q286314_Sequence_Listing_As_Filed.TXT; size: 73,860 bytes; and date of creation: Mar. 23, 2023, is hereby incorporated by reference in their entirety.

TECHNICAL FIELD

The present invention relates to therapeutic uses, for bone diseases, of a triple agonist having activities for all of glucagon, GLP-1, and GIP receptors and/or a long-acting conjugate thereof.

BACKGROUND ART

Bone modeling and remodeling play important roles in the development, growth, and metabolism of bones. Bone modeling begins in fetal life and continues until early adulthood when the skeleton is matured and growth ends, and the maximum bone mass is formed in the ages of between 20 to early 30s. Thereafter, bone remodeling, which involves bone removal and bone supplementation, is repeated for about 30 years, during which bone formation and bone resorption are paired and balanced. After this period, bone formation cannot sufficiently compensate for bone loss due to bone resorption, resulting in a reduction in bone quantity of about 0.3% to about 0.5% per year, and particularly, women experience a considerable bone loss of 2-3% per year in the early stage of menopause.

Bone tissue consists of the cartilage and skeletal system, plays a role in mechanical support and muscle attachment, protects living organs and bone marrow, and is responsible for preserving calcium and phosphorus ions to maintain the homeostasis thereof. Bone tissue consists of the cell matrix, such as collagen and glycoproteins, and various types of cells, including osteoblasts, osteoclasts, and bone cells. Osteoblasts derived from bone marrow stromal cells play a major role in bone formation, and osteoclasts derived from stem cells are responsible for the absorption of the destroyed and aged bone, so that bone remodeling is maintained through a balanced action between bone formation and bone resorption. However, excessive activity of osteoclasts or decreased activity of osteoblasts results in an imbalance in the remodeling process of bone formation, and thus the equilibrium between osteoclasts and osteoblasts in vivo is broken to cause bone diseases.

Osteoporosis, which is a representative example of bone disease, is an unavoidable symptom for the elderly, especially postmenopausal women, to a greater or lesser extent, and there is a gradually increasing interest in osteoporosis and its therapeutic agents as the population ages in developed countries. Osteoporosis refers to a condition in which the bone density is significantly reduced compared to normal people, and osteoporosis is a common metabolic disease where bones are not able to withstand body weight or mechanical pressure and are easily broken from even minor impacts, such as falling down indoors. The bones in our body repeat bone formation of bone resorption and generation, and osteoporosis is considered to be caused by an imbalance between bone modeling and bone resorption. That is, osteoporosis occurs when the amount of bone production cannot keep up with the amount of bone resorption due to the increased bone absorption rate or the decreased bone generation rate, and it is known that after the late 30s, the bone resorption rate becomes faster than the bone generation rate with aging, causing a gradual decrease in bone mass, resulting in gradual weakening of bones. In order to treat osteoporosis, medicines are being developed to maintain the current bone mass by increasing bone formation or preventing bone loss. As for a medicine that inhibits bone resorption, bisphosphonate (Can Fam Physician. 2014 April; 60(4): 324-333), calcitonin, or estrogen is used, and parathyroid hormone is used to increase bone formation.

DISCLOSURE

Technical Problem

The development of practical and effective medicines for bone diseases is not sufficient so far, and thus there is a need for continuous development of medicines.

Technical Solution

An aspect of the present invention is to provide a pharmaceutical composition for prevention or treatment of a bone disease, the pharmaceutical composition containing a peptide having activities for glucagon, glucagon-like peptide-1 (GLP-1), and Glucose-dependent insulinotropic polypeptide (GIP) receptors or a long-acting conjugate of the peptide.

Another aspect of the present invention is to provide a food composition for preventing or alleviating a bone disease, the food composition containing a peptide having activities for glucagon, GLP-1, and GIP receptors or a long-acting conjugate of the peptide.

Still another aspect of the present invention is to provide a method for prevention or treatment of a bone disease, the method including administering to a subject in need thereof the peptide or a long-acting conjugate of the peptide, or a composition containing the peptide or the long-acting conjugate.

Still another aspect of the present invention is to provide use of the peptide or a long-acting conjugate of the peptide or a composition containing the peptide or the long-acting conjugate in the preparation of a medicine for prevention or treatment of a bone disease.

Advantageous Effects

The triple agonists or long-acting conjugates thereof according to the present invention have activities for glucagon, GLP-1, and GIP receptors and thus can be applied to the treatment of bone-related diseases including osteoporosis.

BRIEF DESCRIPTION OF DRAWINGS

FIG. 1 shows serum PINP levels in ovariectomized rats corresponding to an osteoporosis model after a long-acting conjugate of the triple agonist of SEQ ID NO: 42 was consecutively administered to the rats once every three days for 4 weeks. For the purpose of comparison of effects, liraglutide known as a GLP-1 agonist was administered twice a day (*p<0.05, p<0.01, *p<0.001, vs. vehicle control by one-way ANOVA).

FIG. 2 shows serum osteocalcin levels in ovariectomized rats corresponding to an osteoporosis model after a long-acting conjugate of the triple agonist of SEQ ID NO: 42 was consecutively administered to the rats once every three days for 4 weeks. For the purpose of comparison of effects, liraglutide known as a GLP-1 agonist was administered twice a day (*p<0.05, p<0.01, *p<0.001, vs. vehicle control by one-way ANOVA).

FIG. 3 shows the results examining mRNA expression levels of RUNX2, OCN, ALP, and ColA1, which were osteoblast differentiation genes, after MC3T3-E1 osteoblasts were treated with the long-acting conjugate of SEQ ID NO: 42 (*p<0.05, p<0.01, *p<0.001, vs. vehicle control by one-way ANOVA).

FIG. 4 shows the results examining protein expression levels of ColA1 after MC3T3-E1 osteoblasts were treated with the long-acting conjugate of SEQ ID NO: 42 (*p<0.05, p<0.01, *p<0.001, vs. vehicle control by one-way ANOVA).

FIG. 5 shows the results examining cell viability of MC3T3-E1 osteoblasts according to the treatment with the long-acting conjugate of SEQ ID NO: 42 (*p<0.05, p<0.01, *p<0.001, vs. vehicle control by one-way ANOVA).

BEST MODE FOR CARRYING OUT THE INVENTION

In accordance with an aspect of the present invention, there is provided a pharmaceutical composition for prevention or treatment of a bone disease, the pharmaceutical composition containing a peptide having activities for glucagon, glucagon-like peptide-1 (GLP-1), and glucose-dependent insulinotropic polypeptide (GIP) receptors.

In an embodiment, the pharmaceutical composition for prevention or treatment of a bone disease contains: a pharmaceutically acceptable vehicle; and a pharmaceutically effective amount of a peptide containing an amino acid sequence of any one of SEQ ID NOS: 1 to 102.

In the pharmaceutical composition according to any one of the previous embodiments, the peptide is in the form of a long-acting conjugate, wherein the long-acting conjugate is represented by Formula 1 below:

X-L-F [Formula 1]

wherein X represents a peptide containing an amino sequence of any one of SEQ ID NOS: 1 to 102;

L represents a linker containing ethylene glycol repeat units;

F represents an immunoglobulin Fc region; and

"-" symbols represent covalent linkages between X and L and between L and F, respectively.

In the composition according to any one of the previous embodiments, the C-terminus of the peptide is amidated.

In the composition according to any one of the previous embodiments, the C-terminus of the peptide is amidated or has a free carboxyl group (—COOH).

In the composition according to any one of the previous embodiments, the peptide contains an amino acid sequence selected from the group consisting of SEQ ID NOS: 21, 22, 42, 43, 50, 64, 66, 67, 70, 71, 76, 77, 96, 97, and 100.

In the composition according to any one of the previous embodiments, the peptide contains an amino acid sequence selected from the group consisting of SEQ ID NOS: 21, 22, 42, 43, 50, 66, 67, 77, 96, 97, and 100.

In the composition according to any one of the previous embodiments, the peptide contains an amino acid sequence selected from the group consisting of SEQ ID NOS: 21, 22, 42, 43, 50, 77, and 96.

In the composition according to any one of the previous embodiments, the amino acids at positions 16 and 20 form the N-terminus in the peptide sequence form a ring.

In the composition according to any one of the previous embodiments, L is polyethylene glycol.

In the composition according to any one of the previous embodiments, the formula weight of an ethylene glycol repeat unit moiety is in a range of 1 to 100 kDa.

In the composition according to any one of the previous embodiments, F is an IgG Fc region.

In the composition according to any one of the previous embodiments, the immunoglobulin Fc region is aglycosylated.

In the composition according to any one of the previous embodiments, the immunoglobulin Fc region is selected from the group consisting of: (a) a CH1 domain, a CH2 domain, a CH3 domain, and a CH4 domain; (b) a CH1 domain and a CH2 domain; (c) a CH1 domain and a CH3 domain; (d) a CH2 domain and a CH3 domain; (e) a combination between one or at least two domains among a CH1 domain, a CH2 domain, a CH3 domain, and a CH4 domain and an immunoglobulin hinge region or a part of the hinge region; and (f) a dimer between each domain of a heavy chain constant region and a light chain constant region.

In the composition according to any one of the previous embodiments, the immunoglobulin Fc region is a native Fc derivative in which a region capable of forming a disulfide bond is deleted, some amino acids in the N-terminus is deleted, a methionine residue is added to the N-terminus, a complement-binding site is deleted, or an antibody dependent cell mediated cytotoxicity (ADCC) site is deleted.

In the composition according to any one of the previous embodiments, the immunoglobulin Fc region is derived from IgG, IgA, IgD, IgE, or IgM.

In the composition according to any one of the previous embodiments, the immunoglobulin Fc region is a hybrid of domains with different origins derived from an immunoglobulin selected from the group consisting of IgG, IgA, IgD, IgE, and IgM.

In the composition according to any one of the previous embodiments, the immunoglobulin Fc region has a dimeric form.

In the composition according to any one of the previous embodiments, the immunoglobulin Fc region is a dimer consisting of two polypeptide chains, and one end of L is linked only to one of the two polypeptide chains.

In the composition according to any one of the previous embodiments, the immunoglobulin Fc region is an IgG4 Fc region.

In the composition according to any one of the previous embodiments, the immunoglobulin Fc region is an aglycosylated Fc region derived from human IgG4.

In the composition according to any one of the previous embodiments, the immunoglobulin Fc region has a structure in which two polypeptide chains are linked through a disulfide bond, wherein two polypeptide chains are linked through only a nitrogen atom of one of the two chains.

In the composition according to any one of the previous embodiments, the immunoglobulin Fc region includes a monomer of the amino acid sequence of SEQ ID NO: 123.

In the composition according to any one of the previous embodiments, the immunoglobulin Fc region is a homodimer of monomers of the amino acid sequence of SEQ ID NO: 123.

In the composition according to any one of the previous embodiments, the immunoglobulin Fc region is linked through a nitrogen atom of proline at the N-terminus.

In the composition according to any one of the previous embodiments, F, which is an immunoglobulin Fc region, and X are aglycosylated.

In the composition according to any one of the previous embodiments, the ethylene glycol repeat units correspond to $[OCH_2CH_2]n$ where n is a natural number, wherein n is determined such that the average molecular weight, for example, the number average molecular weight, of the $[OCH_2CH_2]n$ moiety in the peptide conjugate is 1 to 100 kDa.

In the composition according to any one of the previous embodiments, the value of n is determined such that the average molecular weight, for example, the number average molecular weight, of the $[OCH_2CH_2]n$ moiety in the peptide conjugate is 10 kDa.

In the composition according to any one of the previous embodiments, in the conjugate, one end of L is linked to F via a covalent linkage formed by reaction with an amine or thiol group of F, and the other end of L is linked to X via a covalent linkage formed by reaction with an amine or thiol group of X.

In the composition according to any one of the previous embodiments, L is polyethylene glycol.

In the composition according to any one of the previous embodiments, the bone disease is osteoporosis, fracture, osteosclerosis, osteopetrosis, arthritis, Paget's disease, periodontal disease, osteogenesis imperfecta, or osteopenia.

In the composition according to any one of the previous embodiments, the bone disease is osteopenia.

In the composition according to any one of the previous embodiments, the pharmaceutical composition, when administered, has one or more of the following characteristics:

(i) reducing serum osteocalcin levels; or (ii) increasing serum procollagen I intact N-terminal propeptide (PINP) levels.

In the composition according to any one of the previous embodiments, the pharmaceutical composition has one or more of the following characteristics:

(i) increasing osteoblast differentiation; or (ii) increasing viability of osteoblasts.

In accordance with another aspect of the present invention, there is provided a method for preventing or treating a bone disease, the method including administering to a subject in need thereof the peptide or a long-acting conjugate of the peptide or a composition containing the peptide or the long-acting conjugate.

In accordance with another aspect of the present invention, there is provided use of the peptide or a long-acting conjugate of the peptide or a composition containing the peptide or the long-acting conjugate in the preparation of a medicine for prevention or treatment of a bone disease.

In accordance with another aspect of the present invention, there is provided use of the peptide or a long-acting conjugate of the peptide or a composition containing the peptide or the long-acting conjugate for the prevention or treatment of a bone disease.

MODE FOR CARRYING OUT THE INVENTION

Hereinafter, the present invention will be described in detail.

Each description and embodiment disclosed in this disclosure may also be applied to other descriptions and embodiments. That is, all combinations of various elements disclosed in this disclosure fall within the scope of the present disclosure. Furthermore, the scope of the present invention is not limited by the specific description below.

Furthermore, those skilled in the art will recognize, or be able to ascertain, by using no more than routine experimentation, many equivalents to the specific embodiments of the invention described herein. Furthermore, these equivalents are intended to be included in the present invention.

Throughout the description herein, not only the typical one-letter and three-letter codes for naturally occurring amino acids, but also three-letter codes generally allowed for other amino acids, such as 2-aminoisobutyric acid (Aib), N-methylglycine (Sar), and α-methyl-glutamic acid, are used. The amino acids mentioned in abbreviations herein are described according to the IUPAC-IUB rules:

Herein, "Aib" may be used interchangeably with "2-aminoisobutyric acid" or "aminoisobutyric acid", and 2-aminoisobutyric acid and aminoisobutyric acid may be used interchangeably with each other.

alanine (Ala, A), arginine (Arg, R)
asparagine (Asn, N), aspartic acid (Asp, D)
cysteine (Cys, C), glutamic acid (Glu, E)
glutamine (Gln, Q), glycine (Gly, G)
histidine (His, H), isoleucine (Ile, I)
leucine (Leu, L), lysine (Lys, K)
methionine (Met, M), phenylalanine (Phe, F)
proline (Pro, P), serine (Ser, S)
threonine (Thr, T), tryptophan (Trp, W)
tyrosine (Tyr, Y), valine (Val, V)

In accordance with an aspect of the present invention, there is provided a pharmaceutical composition for prevention or treatment of a bone disease, the pharmaceutical composition containing a peptide having activities for glucagon, glucagon-like peptide-1 (GLP-1), and glucose-dependent insulinotropic polypeptide (GIP) receptors. Specifically, the bone disease may be a bone metabolic disease or osteopenia, but is not particularly limited thereto.

In an embodiment, the peptide may contain an amino acid sequence of any one of SEQ ID NOS: 1 to 102.

In an embodiment, the pharmaceutical composition for prevention or treatment of a bone disease contains: a pharmaceutically acceptable vehicle; and a pharmaceutically effective amount of a peptide containing an amino acid sequence of any one of SEQ ID NOS: 1 to 102.

The composition of the present invention may contain a pharmaceutically effective amount of a peptide having activities for glucagon, GLP-1, and GIP receptors, and specifically may contain a pharmaceutically effective amount of a peptide (a triple agonist) containing, consisting essentially of, or consisting of at least one sequence of the amino acid sequences of SEQ ID NOS: 1 to 102, but is not limited thereto.

The "peptide having activities for glucagon, GLP-1, and GIP receptors" may be used interchangeably with the term "triple agonist" or "triple agonist peptide". The triple agonist of the present invention may include a peptide containing at least one of the amino acid sequences of SEQ ID NOS: 1 to 102. Alternatively, a peptide consisting essentially of or consisting of any one of the amino acid sequences of SEQ ID NOs: 1 to 102 may also be included in the triple agonist of the present invention, but is not limited thereto. The peptide containing an amino acid sequence of any one of SEQ ID NOS: 1 to 102 is an example of the peptide having activities for glucagon, GLP-1, and GIP receptors, but is not limited thereto.

This peptide encompasses various substances, such as various peptides, with significant levels of activities for glucagon, GLP-1, and GIP receptors.

The triple agonist having significant levels of activities for glucagon, GLP-1, and GIP receptors may exhibit in vitro activities for one or more receptors, specifically two or more receptors, and more specifically all three of the receptors among glucagon, GLP-1, and GIP receptors, of about 0.001% or more, about 0.01% or more, about 0.1% or more, about 1% or more, about 2% or more, about 3% or more, about 4% or more, about 5% or more, about 6% or more, about 7% or more, about 8% or more, about 9% or more, about 10% or more, about 20% or more, about 30% or more, about 40% or more, about 50% or more, about 60% or more, about 70% or more, about 80% or more, about 90% or more, about 100% or more, about 150% or more, or about 200% or more, compared with native ligands (native glucagon, native GLP-1, and native GIP) for the corresponding receptors, but significantly increasing ranges are included without limitation.

The activities for the receptors may include, for example, those cases where the in vitro activities for the receptor are about 0.001% or more, about 0.01% or more, about 0.1% or more, about 1% or more, about 2% or more, about 3% or more, about 4% or more, about 5% or more, about 6% or more, about 7% or more, about 8% or more, about 9% or more, about 10% or more, about 20% or more, about 30% or more, about 40% or more, about 50% or more, about 60% or more, about 70% or more, about 80% or more, about 90% or more, about 100% or more, or about 200% or more, compared with the native ligands. However, the activities for the receptors are not limited thereto.

As used herein, the term "about" refers to a range including ±0.5, ±0.4, ±0.3, ±0.2, ±0.1, and the like, and thus includes all of the values in the range equivalent or similar to those stated after this term, but is not limited thereto.

Methods for measuring the in vitro activities of triple agonists may refer to Test Example 1 herein, but are not particularly limited thereto.

Meanwhile, the peptide retains one or more, two or more, and specifically three of the following activities of i) to iii) below, specifically significant activities thereof:

i) activating the GLP-1 receptor; ii) activating the glucagon receptor; and iii) activating the GIP receptor.

In particular, the activation of the receptors may include, for example, those cases where the in vitro activities for the receptors are about 0.001% or higher, about 0.01% or higher, about 0.1% or higher, about 1% or higher, about 2% or higher, about 3% or higher, about 4% or higher, about 5% or higher, about 6% or higher, about 7% or higher, about 8% or higher, about 9% or higher, about 10% or higher, about 20% or higher, about 30% or higher, about 40% or higher, about 50% or higher, about 60% or higher, about 70% or higher, about 80% or higher, about 90% or higher, about 100% or higher, about 150% or higher, or about 200% or more, compared with native ligands. However, the immunoglobulin Fc region of the present invention is not limited thereto.

The peptide may have an increased in vivo half-life compared with any one of native GLP-1, native glucagon, and native GIP, but is not particularly limited thereto.

Although not particularly limited, the peptide may be a non-naturally occurring peptide.

Although described as a peptide "consisting of" a specific SEQ ID NO herein, such description does not exclude a mutation that may occur by the addition of a meaningless sequence upstream or downstream of the amino acid sequence of the corresponding SEQ ID NO, or a mutation that may occur naturally, or a silent mutation thereof, as long as the peptide has an activity identical or corresponding to that of the peptide consisting of the amino acid sequence of the corresponding SEQ ID NO, and it would be obvious that even a peptide with such a sequence addition or mutation falls within the scope of the present invention. In other words, if a peptide shows at least a certain level of homology and exhibits activities for glucagon, GLP-1, and GIP receptors despite having some sequence differences, such a peptide may fall within the scope of the present invention.

The above description can be applied to other embodiments or aspects of the present invention, but is not limited thereto.

For example, reference may be made to WO 2017-116204 and WO 2017-116205 for the peptide of the present invention.

For example, the peptide of the present invention may also include a peptide containing an amino acid sequence of any one of SEQ ID NOS: 1 to 102, consisting (essentially) of any one of amino acid sequences of SEQ ID NOS 1 to 102, or having sequence identity of at least 60%, 65%, 70%, 75%, 80%, 85%, 90%, 91%, 92%, 93%, 94% or 95% with an amino acid sequence of any one of SEQ ID NOS: 1 to 102, and such an amino acid sequence is not limited to specific sequences as long as they have an effect of treating and/or preventing a bone disease.

Examples of the triple agonist may include a triple agonist containing an amino acid sequence selected from the group consisting of SEQ ID NOS: 1 to 102, a triple agonist containing an amino acid sequence selected from the group consisting of SEQ ID NOS: 1 to 11 and 13 to 102, and a triple agonist containing an amino acid sequence selected from the group consisting (essentially) of an amino acid sequence selected from the group consisting of SEQ ID NO: 1 to 11 and 13 to 102, but are not limited thereto.

As a specific example, the triple agonist peptide may contain, consist essentially of, or consist of an amino acid sequence of any one of SEQ ID NOS: 21 to 24, 28, 29, 31, 32, 37, 42, 43, 50, 51 to 54, 56, 58, 64 to 73, 75 to 79, 82, 83, 91, and 96 to 102, but is not limited thereto. As an example, the triple agonist peptide may contain, consist essentially of, or consist of an amino acid sequence of any one of SEQ ID NOS: 21, 22, 42, 43, 50, 64, 66, 67, 70, 71, 76, 77, 96, 97, and 100, but is not limited thereto.

As another example, the peptide may contain, consist essentially of, or consist of an amino acid sequence of any one of SEQ ID NOS: 21, 22, 42, 43, 50, 66, 67, 77, 96, 97, and 100, but is not limited thereto.

As still another example, the peptide may contain, consist essentially of, or consist of an amino acid sequence of any one of SEQ ID NOS: 21, 22, 42, 43, 50, 77, and 96, but is not limited thereto.

As used herein, the term "homology" or "identity" refers to a degree of relevance between two given amino acid sequences or nucleotide sequences, and the term may be expressed as a percentage.

The terms homology and identity may be often used interchangeably with each other.

The homology, similarity, or identity between any two peptide sequences may be determined by, for example, a known computer algorithm, such as the "FASTA" program, by using default parameters as in Pearson et al (1988) [Proc.

Natl. Acad. Sci. USA 85]: 2444. Alternatively, these may be determined using the Needleman-Wunsch algorithm (Needleman and Wunsch, 1970, J. Mol. Biol. 48: 443-453), which is performed in the Needleman program of the European Molecular Biology Open Software Suite (EMBOSS) package (Rice et al., 2000, Trends Genet. 16: 276-277) (version 5.0.0 or versions thereafter) (GCG program package (including GCG program package (Devereux, J., et al, Nucleic Acids Research 12: 387 (1984)), BLASTP, BLASTN, FASTA (Atschul, [S.] [F.,] [ET AL, J MOLEC BIOL 215]: 403 (1990); Guide to Huge Computers, Martin J. Bishop, [ED.,] Academic Press, San Diego, 1994, and [CARILLO ETA/.](1988) SIAM J Applied Math 48: 1073). For example, the homology, similarity, or identity may be determined using BLAST of the National Center for Biotechnology Information database, or ClustalW.

The homology, similarity, or identity between polypeptides may be determined by comparing sequence information using the GAP computer program, for example, Needleman et al., (1970), J Mol Biol. 48:443, as known in Smith and Waterman, Adv. Appl. Math (1981) 2:482. Briefly, the GAP program defines similarity as the number of aligned symbols (i.e., amino acids) which are similar, divided by the total number of symbols in a shorter of two sequences. Default parameters for the GAP program may include: (1) a binary comparison matrix (containing a value of 1 for identity and 0 for non-identity) and a weighted comparison matrix of Gribskov et al. (1986) Nucl. Acids Res. 14:6745 as disclosed in Schwartz and Dayhoff, eds., Atlas of Protein Sequence and Structure, National Biomedical Research Foundation, pp. 353-358 (1979) (or the EDNAFULL (EMBOSS version of NCBI NUC4.4) substitution matrix); (2) a penalty of 3.0 for each gap and an additional 0.10 penalty for each symbol in each gap (or a gap open penalty of 10, and a gap extension penalty of 0.5); and (3) no penalty for end gaps. Therefore, the term “homology” or “identity” used herein represents the relevance between sequences.

The peptide having activities for glucagon, GLP-1, and GIP receptors may include an intramolecular bridge (e.g., a covalent bridge or non-covalent bridge) and, specifically, may be in the form of including a ring, for example, may be in the form of including a ring formed between the amino acids at positions 16 and 20 in the peptide, but the peptide is not particularly limited thereto.

Non-limiting examples of the ring may include a lactam bridge (or a lactam ring).

Additionally, the peptide includes all of those which are modified to include a ring, or to include amino acids capable of forming a ring at a target site.

For example, the pair of the amino acids at positions 16 and 20 in the peptide may be substituted with glutamic acid or lysine, which can form a ring, but the peptide is not limited thereto.

Such a ring may be formed between side chains of amino acids in the peptide, for example, in the form of a lactam ring formed between a side chain of lysine and a side chain of glutamic acid, but is not particularly limited thereto.

Examples of the peptide prepared by a combination of these methods include a peptide, of which the amino acid sequence differs from that of native glucagon in at least one amino acid, from which α-carbon of the amino acid residue at the N-terminus is deleted, and retains activities for glucagon, GLP-1, and GIP receptors, but are not limited thereto. Peptides applicable to the present invention may be prepared by combining various methods for the preparation of analogs.

Additionally, the peptide of the present invention may have the substitution of some amino acids with other amino acids or non-native compounds in order to avoid the recognition by an agonist protease to increase the in vivo half-life of the peptide, but is not particularly limited thereto.

Specifically, the peptide of the present invention may be a peptide in which the in vivo half-life is increased by avoiding the recognition by a protease through a substitution of the second amino acid in the amino acid sequence of the peptide, but any substitution or change of amino acids to avoid the recognition by an in vivo protease is included without limitation.

Such a modification for peptide preparation includes all of: modifications using L-type or D-type amino acids and/or non-native amino acids; and/or modifications of a native sequence, for example, a variation of a side chain functional group, an intramolecular covalent linkage (e.g., ring formation between side chains), methylation, acylation, ubiquitination, phosphorylation, aminohexanation, biotinylation, or the like.

In addition, such a variation also includes all those where one or more amino acids are added to the amino and/or carboxy terminus of native glucagon.

Regarding the substitution or addition of amino acids, not only the 20 amino acids commonly found in human proteins, but also atypical or non-naturally occurring amino acids may be used. Commercial sources of atypical amino acids may include Sigma-Aldrich, ChemPep, and Genzyme Pharmaceuticals. The peptides including these amino acids and typical peptide sequences can be synthesized and purchased from commercial peptide suppliers, for example, American Peptide Company and Bachem in USA, or Anygen in Korea.

Amino acid derivatives may also be accessible in a similar manner, and for example, 4-imidazoacetic acid or the like may be used.

The peptide according to the present invention may be in a varied form in which the N-terminus and/or C-terminus is chemically modified or protected by organic groups, or amino acids are added to the terminus of the peptide, for its protection from proteases in vivo while increasing its stability.

In particular, a chemically synthesized peptide has electrically charged N- and C-termini, and thus for elimination of these charges, the N-terminus may be acetylated and/or the C-terminus may be amidated, but the peptide is not particularly limited thereto.

Specifically, the N-terminus or the C-terminus of the peptide of the present invention may have an amine group (—NH2) or a carboxy group (—COOH), but is not limited thereto.

The peptide according to the present invention may include a peptide, of which the C-terminus is amidated or has a free carboxy (—COOH) group, or a peptide, of which the C-terminus is not modified, but is not limited thereto.

In an embodiment, the C-terminus of the peptide may be amidated, but is not limited thereto.

In an embodiment, the peptide may be aglycosylated, but is not limited thereto.

The peptide of the present invention may be synthesized through solid-phase synthesis, produced by a recombinant method, or prepared by a commercial request, but is not limited thereto.

In addition, the peptide of the present invention may be synthesized depending on the length thereof by a method well known in the art, for example, an automatic peptide synthesizer, and may be produced by genetic engineering technology.

Specifically, the peptide of the present invention may be prepared by a standard synthesis method, a recombinant expression system, or any other method known in the art. Hence, the peptide according to the present invention may be synthesized by a number of methods including, for example, the following:

(a) a method in which the peptide is synthesized by means of a solid-phase or liquid-phase method either stepwise or by fragment assembling and a final peptide product is isolated and purified;

(b) a method in which a nucleic acid construct encoding a peptide is expressed in a host cell and an expression product is collected from a host cell culture;

(c) a method in which the in vitro cell-free expression of a nucleic acid construct encoding a peptide is performed and an expression product is collected therefrom; or a method in which peptide fragments are obtained by any combination of (a), (b), and (c), the fragments are linked to obtain a peptide, and then the corresponding peptide is collected.

In addition, the peptide having activities for glucagon, GLP-1, and GIP receptors may be in the form of a long-acting conjugate in which a biocompatible substance for increasing the in vivo half-life of a peptide is bound to a peptide having activities for glucagon, GLP-1, and GIP receptors. Herein, the biocompatible substance may be used interchangeably with a carrier. The peptide contained in the pharmaceutical composition of the present invention may be in the form of a long-acting conjugate.

In the present invention, the conjugate of the peptide can exhibit an increase in the duration of efficacy compared with the peptide to which a carrier is not bound, and in the present invention, such a conjugate is referred to as a "long-acting conjugate".

Such a conjugate may be a non-naturally occurring conjugate.

In a specific embodiment of the present invention, the long-acting conjugate refers to a form in which an immunoglobulin Fc region is linked to a peptide having activities for glucagon, GLP-1, and GIP receptors. Specifically, the conjugate may be a conjugate in which an immunoglobulin Fc region is covalently linked to a peptide having activities for glucagon, GLP-1, and GIP receptors via a linker, but is not particularly limited thereto.

In an embodiment of the present invention, the long-acting conjugate may be represented by Formula 1 below, but is not limited thereto:

X-L-F [Formula 1]

wherein X represents a peptide containing an amino sequence of any one of SEQ ID NOS: 1 to 102;

L represents a linker containing ethylene glycol repeat units;

F represents an immunoglobulin Fc region; and

"-" symbols represent covalent linkages between X and L and between L and F, respectively.

Herein, the term "long-acting conjugate of Formula 1" refers to a form in which a peptide containing an amino acid sequence of any one of SEQ ID NOS: 1 to 102 is linked to an immunoglobulin Fc region via a linker, and the conjugate may exhibit an increase in the duration of efficacy compared with a peptide containing an amino acid sequence of any one of the amino acid sequences of SEQ ID NOS: 1 to 102, to which the immunoglobulin Fc region is not bound.

The conjugate of the present invention, even in the form of a conjugate, can exhibit significant activities for glucagon, GLP-1, and GIP receptors, and thus can also exert an effect of preventing and/or treating a bone disease.

Specifically, the conjugate of the present invention can exhibit in vitro activities for glucagon, GLP-1, and/or GIP receptors, of about 0.01% or more, about 0.1% or more, about 0.2% or more, about 0.5% or more, about 0.7% or more, about 1% or more, about 2% or more, about 3% or more, about 4% or more, about 5% or more, about 6% or more, about 7% or more, about 8% or more, about 9% or more, about 10% or more, about 20% or more, about 30% or more, about 40% or more, about 50% or more, about 60% or more, about 70% or more, about 80% or more, about 90% or more, or about 100% or more, compared with native forms, but is not limited thereto.

For the purposes of the present invention, the peptide or the conjugate thereof can exhibit activities for glucagon, GLP-1, and/or GIP receptors, of about 0.01% or more, about 0.1% or more, about 1% or more, about 2% or more, about 3% or more, about 4% or more, about 5% or more, about 10% or more, about 20% or more, about 30% or more, about 40% or more, about 50% or more, about 60% or more, about 70% or more, about 80% or more, about 90% or more, or about 100% or more, compared with native forms, but is not limited thereto.

The composition of the present invention may contain (i) a peptide having activities for glucagon, GLP-1, and GIP receptors, or (ii) a long-acting conjugate of the peptide having activities for glucagon, GLP-1, and GIP receptors, and the long-acting conjugate can show an excellent effect of preventing and/or treating a bone disease on the basis of an increase in the in vivo duration of efficacy.

In the long-acting conjugate, F is a substance capable of increasing the half-life of X, that is, a peptide having activities for glucagon, GLP-1, and GIP receptors, specifically, a peptide containing any one sequence of the amino acid sequences of SEQ ID NO: 1 to 102, and corresponds to one element of a moiety constituting the conjugate of the present invention.

F may be bound to X by a covalent chemical linkage or a non-covalent chemical linkage, and F and X may be linked to each other via a linker by a covalent chemical linkage, a non-covalent chemical linkage, or a combination thereof.

As one example, in the conjugate, X and L and L and F may be linked to each other through covalent linkages, respectively, wherein the conjugate may be a conjugate in which X, L, and F are linked to each other through covalent linkages in the form of Formula 1.

Specifically, the method of linking X, which is a peptide containing an amino acid sequence of any one of SEQ ID NOS: 1 to 102, and an immunoglobulin Fc region in the long-acting conjugate of Formula 1 is not particularly limited, but an amino acid sequence of any one of SEQ ID NOS: 1 to 102 and an immunoglobulin Fc region may be linked to each other via a linker.

Specifically, L may be a non-peptide linker, for example, a linker containing ethylene glycol repeat units.

In the present invention, the "non-peptide linker" includes a biocompatible polymer having two or more repeat units linked to each other. The repeat units are linked to each other by any covalent linkage but not a peptide linkage. The non-peptide linker may be one element constituting a moiety of the conjugate of the present invention, and corresponds to L in Formula 1.

As the non-peptide linker usable in the present invention, any polymer that has resistance to in vivo protease may be used without limitation. In the present invention, the non-peptide linker may be used exchangeably with a non-peptide polymer.

In the present invention, the non-peptide linker may include reactive groups at the ends thereof and thus may form a conjugate by reaction with the other elements constituting the conjugate. When the non-peptide linker having reactive functional groups at both ends thereof binds to X and F in Formula 1 through the respective reactive groups to form a conjugate, the non-peptide linker or non-peptide polymer may be named a non-peptide polymer linker moiety or a non-peptide linker moiety.

Although not particularly limited, the non-peptide linker may be a linker containing ethylene glycol repeat units, and for example, may be polyethylene glycol, and derivatives thereof that are already known in the art and derivatives that can be easily prepared within the level of skill in the art also fall within the scope of the present invention.

In the present invention, the "polyethylene glycol linker" includes a biocompatible polymer having two or more repeat units linked to each other. The repeat units are linked to each other by any covalent linkage but not a peptide linkage. The polyethylene glycol linker may be one element constituting a moiety of the conjugate of the present invention, and corresponds to L in Formula 1.

Specifically, L (polyethylene glycol linker) may be a linker containing ethylene glycol repeat units, for example, polyethylene glycol, but is not limited thereto. Herein, the polyethylene glycol is a term encompassing all of the forms of homopolymers of ethylene glycol, PEG copolymers, and monomethyl-substituted PEG polymers (mPEG), but is not particularly limited thereto. In addition, derivatives thereof that are already known in the art and derivatives that can be easily prepared within the skill in the art are also included in the scope of the present invention.

The polyethylene glycol linker may include a functional group used in the preparation of the conjugate before being configured into the conjugate, while including ethylene glycol repeat units. The long-acting conjugate according to the present invention may be in the form in which X and F are linked through the functional group, but is not limited thereto. In the present invention, the non-peptide linker may include two, or three or more functional groups, and each functional group may be the same as or different from each other, but is not limited thereto.

Specifically, the linker may be polyethylene glycol (PEG) represented by Formula 2 below, but is not limited thereto:

[Formula 2]

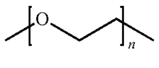

wherein n is 10 to 2400, n is 10 to 480, or n is 50 to 250, but is not limited thereto.

In the long-acting conjugate, the PEG moiety may include not only the $(CH_2CH_2O)_n$ structure, but also an oxygen atom interposed between a linking element and the $(CH_2CH_2O)_n$ structure, but not limited thereto.

In an embodiment, the ethylene glycol repeat units may be represented by, for example, $[OCH_2CH_2]_n$, wherein the value of n is a natural number, and the average molecular weight, for example, the number average molecular weight of the $[OCH_2CH_2]_n$ moiety in the peptide conjugate may be set to more than 0 kDa to about 100 kDa, but is not limited thereto. As another example, the value of n is a natural number, and the average molecular weight, for example, the number average molecular weight of the $[OCH_2CH_2]_n$ moiety in the peptide conjugate may be about 1 to about 100 kDa, about 1 to about 80 kDa, about 1 to about 50 kDa, about 1 to about 30 kDa, about 1 to about 25 kDa, about 1 to about 20 kDa, about 1 to about 15 kDa, about 1 to about 13 kDa, about 1 to about 11 kDa, about 1 to about 10 kDa, about 1 to about 8 kDa, about 1 to about 5 kDa, about 1 to about 3.4 kDa, about 3 to about 30 kDa, about 3 to about 27 kDa, about 3 to about 25 kDa, about 3 to about 22 kDa, about 3 to about 20 kDa, about 3 to about 18 kDa, about 3 to about 16 kDa, about 3 to about 15 kDa, about 3 to about 13 kDa, about 3 to about 11 kDa, about 3 to about 10 kDa, about 3 to about 8 kDa, about 3 to about 5 kDa, about 3 to about 3.4 kDa, about 8 to about 30 kDa, about 8 to about 27 kDa, about 8 to about 25 kDa, about 8 to about 22 kDa, about 8 to about 20 kDa, about 8 to about 18 kDa, about 8 to about 16 kDa, about 8 to about kDa, about 8 to about 13 kDa, about 8 to about 11 kDa, about 8 to about 10 kDa, about 9 to about 15 kDa, about 9 to about 14 kDa, about 9 to about 13 kDa, about 9 to about 12 kDa, about 9 to about 11 kDa, about 9.5 to about 10.5 kDa, or about 10 kDa, but is not limited thereto.

In a specific embodiment, the conjugate may have a structure in which the peptide (X) and the immunoglobulin Fc region (F) are covalently linked via a linker containing ethylene glycol repeat units, but is not limited thereto.

In a specific embodiment, the long-acting conjugate may have a structure in which the peptide (X) and the immunoglobulin Fc region (F) of the present invention are covalently linked via a linker containing ethylene glycol repeat units, but is not limited thereto.

As the non-peptide that can be used in the present invention, any polymer that has a resistance to proteases in vivo and contains an ethylene glycol unit may be used without limitation. The molecular weight of the non-peptide polymer may be in a range of more than 0 kDa to about 100 kDa, or about 1 kDa to about 100 kDa, and specifically about 1 kDa to about 20 kDa, or about 1 kDa to about kDa, but is not limited thereto. In addition, as the non-peptide linker of the present invention, which is bound to the polypeptide corresponding to F, not only a single type of polymer but also a combination of different types of polymers may be used.

In a specific embodiment, both ends of the non-peptide linker may be linked to a thiol group, an amino group, or a hydroxyl group of the immunoglobulin Fc region and a thiol group, an amino group, an azide group, or a hydroxyl group of the peptide (X), respectively, but are not limited thereto.

Specifically, the linker may include, at both ends thereof, reactive groups capable of binding to F (e.g., the immunoglobulin Fc region) and X, respectively, and specifically reactive groups capable of binding to: a thiol group of cysteine, an amino group located at the N-terminus lysine, arginine, glutamine, and/or histidine, and/or a hydroxyl group located at the C-terminus in the immunoglobulin Fc region; and a thiol group of cysteine; an amino group of lysine, arginine, glutamine, and/or histidine; an azide group of azidolysine; and/or a hydroxyl group in the peptide (X), but is not limited thereto.

Alternatively, the reactive groups of the linker, capable of being linked to F, for example, an immunoglobulin Fc region, and X, may be selected from the group consisting of an aldehyde group, a maleimide group, and a succinimide derivative, but are not limited thereto.

In the above description, examples of the aldehyde group may include a propionaldehyde group or a butyraldehyde group, but are not limited thereto.

In the above description, examples of the succinimide derivative may include succinimidyl valerate, succinimidyl methylbutanoate, succinimidyl methylpropionate, succinimidyl butanoate, succinimidyl propionate, N-hydroxysuccinimide, hydroxy succinimidyl, succinimidyl carboxymethyl, and succinimidyl carbonate, but are not limited thereto.

The linker may be converted into a linker moiety by linking to the immunoglobulin Fc region F and the peptide (triple agonist) X via the reactive groups.

In addition, a final product produced by reductive amination through aldehyde linkage is still more stable than a product obtained through amide linkage. The aldehyde reactive group selectively reacts with the N-terminus at low pH while forming a covalent linkage with a lysine residue at high pH, for example, at pH 9.0.

The reactive groups at both ends of the non-peptide linker may be the same as or different from each other, and for example, one end may have a maleimide group, and the other end may have an aldehyde group, a propionaldehyde group, or a butyraldehyde group. However, the reactive groups are not particularly limited thereto as long as F, specifically an immunoglobulin Fc region, and X can be linked to both ends of the non-peptide linker.

For example, the non-peptide linker may have a maleimide group as a reactive group at one end and an aldehyde group, a propionaldehyde group, a butyraldehyde group, or the like at the other end.

When polyethylene glycol having hydroxyl reactive groups at both ends is used as a non-peptide polymer, the long-acting protein conjugate of the present invention may be prepared by activating the hydroxyl groups into various reactive groups through known chemical reactions or by using commercially available polyethylene glycol having modified reactive groups.

In a specific embodiment, the non-peptide polymer may be linked to a cysteine residue of X, more specifically the —SH group of cysteine, but is not limited thereto.

For example, the non-peptide polymer may be linked to the cysteine residue at position 10, the cysteine residue at position 13, the cysteine residue at position 15, the cysteine residue at position 17, the cysteine residue at position 19, the cysteine residue at position 21, the cysteine residue at position 24, the cysteine residue at position 28, the cysteine residue at position 29, the cysteine residue at position 30, the cysteine residue at position 31, the cysteine residue at position 40, or the cysteine residue at position 41 in the peptide corresponding to X, but is not particularly limited.

Specifically, a reactive group of the non-peptide polymer may be linked to the —SH group of the cysteine residue, and all of those described above are applied to the reactive group. When maleimide-PEG-aldehyde is used, the maleimide group may be linked to the —SH group of X through a thioether linkage, and the aldehyde group may be linked to the —NH2 group of F, specifically, the immunoglobulin Fc region through reductive amination, but is not limited thereto.

In the conjugate, the reactive group of the non-peptide polymer may be linked to —NH2 group located at the N-terminus of the immunoglobulin Fc region, but this case corresponds to one example.

When maleimide-PEG-aldehyde is used, the maleimide group may be linked to the —SH group of the peptide through a thioether linkage, and the aldehyde group may be linked to the —NH2 group of the immunoglobulin Fc region through reductive alkylation, but is not limited thereto, and this case corresponds to one example.

Through such reductive alkylation, the N-terminal amino group of the immunoglobulin Fc region is linked to the oxygen atom located at one terminus of the PEG through a linker functional group having a structure of $-CH_2CH_2CH_2-$ to form a structure of -PEG-O—$CH_2CH_2CH_2NH$-immunoglobulin Fc, and through a thioether linkage, a structure in which one terminus of PEG is linked to a sulfur atom located at cysteine of the peptide may be formed. The above-described thioether linkage may contain the structure of

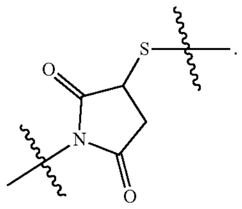 [SMILES: *SC1CC(=O)N(*)C1=O]

However, the non-peptide polymer is not particularly limited to the above example, and this case corresponds to one example.

In the conjugate, the reactive group of the linker may be linked to —NH2 located at the N-terminus of the immunoglobulin Fc region, but this is merely an embodiment.

In the conjugate, the peptide according to the present invention may be linked to a linker having a reactive group through the N-terminus thereof, but this is merely an embodiment.

As used herein, the term "C-terminus" refers to the carboxy terminus of the peptide, and for the purpose of the present invention, the term refers to a position that can be linked to a linker. For example, although not limited, the C-terminus may include not only the amino acid residue at the outermost end of the C-terminus but also amino acid residues near the C-terminus, and specifically, the 1st to 20th amino acid residues from the outermost end.

The above-described conjugate may have an increase in the duration of efficacy compared with conjugates having X not modified with F, and such a conjugate includes not only the above-described form but also a form that is encapsulated in a biodegradable nanoparticle.

Meanwhile, F may be an immunoglobulin Fc region and, more specifically, the immunoglobulin Fc region may be derived from IgG, but is not particularly limited thereto.

In a specific embodiment of the present invention, F (the immunoglobulin Fc region) is a dimer consisting of two polypeptide chains and has a structure in which one end of L is linked to only one polypeptide chain of the two polypeptide chains, but is not limited thereto.

In the present invention, the term "immunoglobulin Fc region" refers to a region that includes heavy chain constant region 2 (CH2) and/or heavy chain constant region 3 (CH3) portions, excluding heavy chain and light chain variable regions in an immunoglobulin. The immunoglobulin Fc region may be one element constituting a moiety of the conjugate of the present invention. The immunoglobulin Fc region may be used interchangeably with the term "immunoglobulin Fc fragment".

Herein, the Fc region includes not only native sequences obtained by papain digestion of immunoglobulins, but also derivatives thereof, for example, variants, such as sequences in which one or more amino acid residues in the native sequence have been altered through deletion, insertion, non-conservative or conservative substitution, or a combination of these and is thus different from that of the native form. The derivatives, modifications, and variants are based on the assumption that these retain the ability to bind to FcRn.

In the present invention, F may be a human immunoglobulin region, but is not limited thereto. Herein, the "biocompatible substance" or "carrier" may mean the Fc region.

F (immunoglobulin Fc region) has a structure in which two polypeptide chains are linked by a disulfide linkage, with the two chains being linked through only a nitrogen atom of one of the chains, but is not limited thereto. The linking through a nitrogen atom may be performed on the epsilon amino group or the N-terminal amino group of lysine through reductive amination.

The term reductive amination refers to a reaction in which an amine group or an amino group of one reactant reacts with an aldehyde (i.e., a functional group capable of reductive amination) of another reactant to form an amine, which then forms an amine linkage by reductive reaction, and this is an organic synthetic reaction that has been widely known in the art.

In an embodiment, F may be linked through a nitrogen atom of the N-terminus proline thereof, but is not limited thereto.

The immunoglobulin Fc region may be one element constituting a moiety of the conjugate of Formula 1 of the present invention, and may correspond to F in Formula 1.

This immunoglobulin Fc region may include a hinge region in the heavy chain constant region, but is not limited thereto.

In the present invention, the immunoglobulin Fc region may include a specific hinge sequence at the N-terminus.

As used herein, the term "hinge sequence" refers to a site which is located on a heavy chain and forms a dimer of the immunoglobulin Fc region through an inter-disulfide bond.

In the present invention, the hinge sequence may be mutated to have only one cysteine residue by deletion of a part in a hinge sequence having the following amino acid sequence, but is not limited thereto:

(SEQ ID NO: 103)
Glu-Ser-Lys-Tyr-Gly-Pro-Pro-Cys-Pro-Ser-Cys-Pro.

The hinge sequence may include only one cysteine residue by deletion of the 8th or 11th cysteine residue in the hinge sequence of SEQ ID NO: 103. The hinge sequence of the present invention may consist of 3 to 12 amino acids including only one cysteine residue, but is not limited thereto. More specifically, the hinge sequence of the present invention may have the following sequence:

(SEQ ID NO: 104)
Glu-Ser-Lys-Tyr-Gly-Pro-Pro-Pro-Ser-Cys-Pro, (SEQ ID NO: 105)
Glu-Ser-Lys-Tyr-Gly-Pro-Pro-Cys-Pro-Ser-Pro, (SEQ ID NO: 106)
Glu-Ser-Lys-Tyr-Gly-Pro-Pro-Cys-Pro-Ser, (SEQ ID NO: 107)
Glu-Ser-Lys-Tyr-Gly-Pro-Pro-Cys-Pro-Pro,

-continued (SEQ ID NO: 108)
Lys-Tyr-Gly-Pro-Pro-Cys-Pro-Ser, (SEQ ID NO: 109)
Glu-Ser-Lys-Tyr-Gly-Pro-Pro-Cys, (SEQ ID NO: 110)
Glu-Lys-Tyr-Gly-Pro-Pro-Cys, (SEQ ID NO: 111)
Glu-Ser-Pro-Ser-Cys-Pro, (SEQ ID NO: 112)
Glu-Pro-Ser-Cys-Pro, (SEQ ID NO: 113)
Pro-Ser-Cys-Pro, (SEQ ID NO: 114)
Glu-Ser-Lys-Tyr-Gly-Pro-Pro-Ser-Cys-Pro, (SEQ ID NO: 115)
Lys-Tyr-Gly-Pro-Pro-Pro-Ser-Cys-Pro, (SEQ ID NO: 116)
Glu-Ser-Lys-Tyr-Gly-Pro-Ser-Cys-Pro, (SEQ ID NO: 117)
Glu-Ser-Lys-Tyr-Gly-Pro-Pro-Cys, (SEQ ID NO: 118)
Lys-Tyr-Gly-Pro-Pro-Cys-Pro, (SEQ ID NO: 119)
Glu-Ser-Lys-Pro-Ser-Cys-Pro, (SEQ ID NO: 120)
Glu-Ser-Pro-Ser-Cys-Pro, (SEQ ID NO: 121)
Glu-Pro-Ser-Cys, (SEQ ID NO: 122)
Ser-Cys-Pro.

More specifically, the hinge sequence may contain an amino acid sequence of SEQ ID NO: 113 (Pro-Ser-Cys-Pro) or SEQ ID NO: 122 (Ser-Cys-Pro), but is not limited thereto.

The immunoglobulin Fc region of the present invention may be in the form in which two molecules of the immunoglobulin Fc chain form a dimer due to the presence of a hinge sequence, and the conjugate of Formula 1 of the present invention may be in the form in which one terminus of the linker is linked to one chain of the dimeric immunoglobulin Fc region, but is not limited thereto.

As used herein, the term "N-terminus" refers to an amino terminus of a protein or polypeptide, and may include the outermost end of the amino terminus, or 1, 2, 3, 4, 5, 6, 7, 8, 9, or 10 or more amino acids from the outermost end. In the immunoglobulin Fc region of the present invention, a hinge sequence may include in the N-terminus, but is not limited thereto.

The immunoglobulin Fc region of the present invention may be an extended Fc region including a part or the entirety of heavy chain constant region 1 (CH1) and/or light chain constant region 1 (CL1), excluding only heavy chain and light chain variable regions of an immunoglobulin, as long as the immunoglobulin Fc region has a substantially equivalent or improved effect compared with the native form. Alternatively, the immunoglobulin Fc region of the present invention may be a region in which a considerably long part of the amino acid sequence corresponding to CH2 and/or CH3 is deleted.

For example, the immunoglobulin Fc region of the present invention may be 1) a CH1 domain, a CH2 domain, a CH3 domain, and a CH4 domain; 2) a CH1 domain and a CH2 domain; 3) a CH1 domain and a CH3 domain; 4) a CH2 domain and a CH3 domain; 5) a combination of one or more domains among a CH1 domain, a CH2 domain, a CH3 domain, and a CH4 domain and an immunoglobulin hinge region (or a part of the hinge region); and 6) a dimer of each domain of a heavy chain constant region and a light chain constant region, but is not limited thereto. However, the immunoglobulin Fc region of the present invention is not limited thereto.

In the present invention, the immunoglobulin Fc region may be in the form of a dimer or multi-mer consisting of single-chain immunoglobulins consisting of domains of the same origin, but is not limited thereto.

In an embodiment, the immunoglobulin Fc region may be in a dimeric form, and one molecule of X may be covalently linked to one Fc region in a dimeric form, wherein the immunoglobulin Fc and X may be linked to each other by a non-peptide polymer. In an embodiment of the long-acting conjugate of the present invention, the immunoglobulin Fc region F is a dimer consisting of two polypeptide chains, wherein the dimeric Fc region F and X may be covalently linked to each other via one identical linker L containing ethylene glycol repeat units. In a specific embodiment, X is covalently linked only to one polypeptide chain of the two polypeptide chains of the dimeric Fc region F via the linker L. In a more specific embodiment, only one molecule of X may be covalently linked via L to one polypeptide chain, to which X is linked, of the two polypeptide chains of the dimeric Fc region F. In a most specific embodiment, F is a homodimer.

In another embodiment, the immunoglobulin Fc region F may be a dimer consisting of two polypeptide chains, wherein one end of L is linked only to one polypeptide chain of the two polypeptide chains, but is not limited thereto.

In another embodiment of the long-acting conjugate of the present invention, two molecules of X may be symmetrically bound to one Fc region in a dimeric form. The immunoglobulin Fc and X may be linked to each other via a non-peptide linker. However, the present invention is not limited to the above-described embodiments.

The immunoglobulin Fc region of the present invention includes not only the native amino acid sequence as well as a derivative thereof. The derivative of the native amino acid sequence means an amino acid sequence which is different from the native amino acid sequence by a deletion, an insertion, a non-conservative or conservative substitution, or a combination thereof of one or more amino acid residues in the native amino acid sequence.

For example, the amino acid residues at positions 214 to 238, 297 to 299, 318 to 322, or 327 to 331, which are known to be important for linkage in IgG Fc, may be used as appropriate sites for variation.

In addition, various types of derivatives are possible by, for example, removing a region capable of forming a disulfide bond, deleting some amino acid residues at the N-terminus of native Fc, or adding a methionine residue at the N-terminus of native Fc. In addition, a complement-binding site, for example, a C1q-binding site, may be removed, and an antibody dependent cell mediated cytotoxicity (ADCC) site may be removed to remove effector functions. Techniques for preparing such sequence derivatives of the immunoglobulin Fc region are disclosed in WO 97/34631 and WO 96/32478, and the like.

Amino acid exchanges in proteins and peptides, which do not alter the entire activity of molecules, are well known in the art (H. Neurath, R. L. Hill, The Proteins, Academic Press, New York, 1979). The most commonly occurring exchanges are exchanges between amino acid residues Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and Asp/Gly. In some cases, amino acids may be modified by phosphorylation, sulfation, acrylation, glycosylation, methylation, farnesylation, acetylation, amidation, or the like.

The above-described Fc derivatives exhibit a biological activity equivalent to that of the Fc region of the present invention, and may be obtained by improving the structural stability of the Fc region against heat, pH, and the like.

Such an Fc region may be obtained from native forms isolated from living bodies of humans or animals, such as cows, goats, pigs, mice, rabbits, hamsters, rats, and guinea pigs, or may be recombinant forms or derivatives thereof obtained from transformed animal cells or microorganisms. In particular, the Fc region may be obtained from a native immunoglobulin by isolating a whole immunoglobulin from a living human or animal body and then treating the isolated immunoglobulin with protease. The isolated immunoglobulin is cleaved into Fab and Fc by treatment with papain, and cleaved into pF'c and $F(ab)_2$ by treatment with pepsin. These may be subjected to size-exclusion chromatography or the like to separate Fc or pF'c therefrom. In a more specific embodiment, the immunoglobulin Fc region is a recombinant immunoglobulin Fc region obtained from microorganisms.

In addition, the immunoglobulin Fc region may have native glycans, increased or decreased glycans compared with the native form, or be in a deglycosylated form. The increase, decrease, or removal of the immunoglobulin Fc glycans may be achieved by using conventional methods, such as a chemical method, an enzymatic method, and a genetic engineering method using a microorganism. The immunoglobulin Fc region obtained by removal of glycans from Fc shows a significant deterioration in binding affinity to the complement c1q and a decrease or elimination in antibody-dependent cytotoxicity or complement-dependent cytotoxicity, and thus cause no unnecessary immune response in vivo. In this regard, a deglycosylated or aglycosylated immunoglobulin Fc region may be a more suitable form to meet the original purpose of the present invention as a drug carrier.

As used herein, the term “deglycosylation” means the enzymatic removal of sugars from an Fc region, while the term “aglycosylation” means an unglycosylated Fc region produced in prokaryotes, more specifically, *E. coli.*

Meanwhile, the immunoglobulin Fc region may be originated from humans, or other animals including cows, goats, pigs, mice, rabbits, hamsters, rats, and guinea pigs, and in a more specific embodiment, the immunoglobulin Fc region is originated from humans.

In addition, the immunoglobulin Fc region may be an Fc region derived from IgG, IgA, IgD, IgE, IgM, or a combination or hybrid thereof. In a still more specific embodiment, the immunoglobulin Fc region is derived from IgG or IgM, which is most abundant in the human blood, and in a still more specific embodiment, the immunoglobulin Fc region is derived from IgG, which is known to increase the half-lives of ligand-binding proteins. In a still more specific embodiment, the immunoglobulin Fc region is an IgG4 Fc region, and in a most specific embodiment, the immunoglobulin Fc region is an aglycosylated Fc region derived from human IgG4, but is not limited thereto.

In a specific embodiment, the immunoglobulin Fc region, which is a fragment of human IgG4 Fc, may be in the form of a homodimer in which two monomers are linked through a disulfide bond (inter-chain form) between cysteines, which are the third amino acids of the monomers, respectively. In particular, each monomer of the homodimer independently have/may have an inter-disulfide bond between cysteines at positions 35 and 95 and an inter-disulfide bond between cysteines at positions 141 and 199, that is, two inter-disulfide bonds (intra-chain form). With respect to the number of amino acids, each monomer may consist of 221 amino acids, and the number of the amino acids forming the homodimer may be a total of 442, but the number of amino acids is not limited thereto. Specifically, in the immunoglobulin Fc fragment, two monomers having the amino acid sequence of SEQ ID NO: 123 (consisting of 221 amino acids) form a homodimer through an inter-disulfide bond between cysteines, which are the 3rd amino acid of each monomer, wherein the monomers of the homodimer independently form an inter-disulfide bond between the cysteines at positions 35 and 95 and an inter-disulfide bond between the cysteines at positions 141 and 199, respectively, but the immunoglobulin Fc fragment is not limited thereto.

F in Formula 1 may include a monomer having the amino acid sequence of SEQ ID NO: 123, wherein F may be a homodimer of monomers having the amino acid sequence of SEQ ID NO: 123, but is not limited thereto.

As one example, the immunoglobulin Fc region may be a homodimer containing the amino acid sequence of SEQ ID NO: 134 (consisting of 442 amino acids), but is not limited thereto.

In an embodiment, the immunoglobulin Fc region and X may not be glycosylated, but are not limited thereto.

As used herein, the term "combination" means that when a dimer or multimer is formed, a polypeptide encoding the single-chain immunoglobulin constant region of the same origin (specifically an Fc region) forms a bond with a single-chain polypeptide of different origin. That is, a dimer or multimer may be prepared from two or more fragments selected from the group consisting of IgG Fc, IgA Fc, IgM Fc, IgD Fc, and IgE Fc fragments.

As used herein, the term "hybrid" means that a sequence corresponding to two or more immunoglobulin Fc fragments of different origins is present in a single-chain immunoglobulin constant region. In the present invention, several types of hybrid are possible. That is, the hybrid domain may be composed of one to four domains selected from the group consisting of CH1, CH2, CH3, and CH4 of IgG Fc, IgM Fc, IgA Fc, IgE Fc, and IgD Fc can be hybridized, and may include a hinge region.

Meanwhile, IgG may also be divided into IgG1, IgG2, IgG3, and IgG4 subclasses, and the present invention may also include a combination thereof or a hybridization thereof. Specifically, IgG may be IgG2 and IgG4 subclasses, and more specifically, an Fc fragment of IgG4 rarely having effector functions, such as complement dependent cytotoxicity (CDC).

The above-described conjugate may have an increase in the duration of efficacy compared with native GLP-1, GIP, or glucagon or with X which is not modified with F, and such a conjugate includes not only the above-described form but also a form that is encapsulated in a biodegradable nanoparticle, but is not limited thereto.

The above-described conjugate may have an increase in the duration of efficacy compared with native GLP-1, GIP, or glucagon or with X which is not modified with F, and such a conjugate includes not only the above-described form but also a form that is encapsulated in a biodegradable nanoparticle.

With respect to the above-described triple agonist and the long-acting conjugate thereof, the entire contents of International Patent Publication Nos. WO 2017/116204 and WO 2017/116205 are incorporated herein by reference.

Unless specified otherwise herein, the contents in the detailed description and claims with respect to the "peptide" according to the present invention or a "conjugate" in which this peptide is covalently linked to a biocompatible substance through a covalent linkage are applied to the ranges including all of not only the corresponding peptide or conjugate but also salts of the corresponding peptide or conjugate (e.g., pharmaceutically acceptable salts of the peptide) or solvates thereof. Therefore, although described as only "peptide" or "conjugate" herein, the corresponding described contents are equally applied to a specific salt thereof, a specific solvate thereof, and a specific solvate of the specific salt thereof. These salts may be in the form in which, for example, any pharmaceutically acceptable salt is used. The type of the salt is not particularly limited. However, the salt is preferably in the form that is safe and effective to a subject, e.g., a mammal, but is not particularly limited thereto.

The type of the salt is not particularly limited. However, the salt is preferably in the form that is safe and effective to a subject, e.g., a mammal, but is not particularly limited thereto.

The term "pharmaceutically acceptable" refers to a substance that can be effectively used for a desired purpose without causing excessive toxicity, irritation, allergic responses, and the like within the range of the medical and pharmaceutical decision.

As used herein, the term "pharmaceutically acceptable salt" refers to a salt derived from pharmaceutically acceptable inorganic acids, organic acids, or bases. Examples of appropriate acids may include hydrochloric acid, bromic acid, sulfuric acid, nitric acid, perchloric acid, fumaric acid, maleic acid, phosphoric acid, glycolic acid, lactic acid, salicylic acid, succinic acid, toluene-p-sulfonic acid, tartaric acid, acetic acid, citric acid, methanesulfonic acid, formic acid, benzoic acid, malonic acid, naphthalene-2-sulfonic acid, benzenesulfonic acid, and the like. Salts derived from appropriate bases may include alkali metals such as sodium and potassium, alkali earth metals such as magnesium, ammonium, and the like.

As used herein, the term "solvate" refers to a complex formed between the peptide according to the present invention or a salt thereof and a solvent molecule.

A composition containing the peptide (e.g., the peptide itself or a long-acting conjugate form in which a biocompatible substance is bound to the peptide) may be used for the prevention or treatment of a bone disease.

The composition according to the present invention may contain a peptide (e.g., the peptide itself or a long-acting conjugate form in which a biocompatible substance is bound to the peptide), and specifically may contain a pharmaceutically effective amount of the peptide or a long-acting conjugate thereof. The composition of the present invention may further contain a pharmaceutically acceptable carrier.

As used herein, the term "prevention" refers to any action that inhibit or delay the occurrence of a bone disease by administration of the above peptide (e.g., the peptide itself or a long-acting conjugate form in which a biocompatible substance is bound to the peptide) or a composition containing the peptide, while the term "treatment" refers to any action that alleviates or advantageously change the symptoms of a bone diseases by administration of the above peptide (e.g., the peptide itself or a long-acting conjugate form in which a biocompatible substance is bound to the peptide) or a composition containing the peptide.

As used herein, the term "administration" refers to the introduction of a predetermined substance into a patient by any appropriate method, and the route of administration of the composition may include, but is not particularly limited to, any typical route through which the composition can arrive at a target in vivo, and for example, the route of administration may be intraperitoneal administration, intravenous administration, intramuscular administration, subcutaneous administration, intradermal administration, oral administration, topical administration, intranasal administration, intrapulmonary administration, intrarectal administration, or the like.

The use of the triple agonist and the long-acting conjugate thereof that has activities for all of long-acting glucagon, GLP-1, and GIP receptors can show a remarkable increase in the blood half-life and in vivo duration of efficacy, thereby reducing the frequency of administration to chronic patients suffering from daily injections, leading to an improvement in the quality of life in the patients, and thus the triple agonist and the long-acting conjugate thereof of the present invention helps in the treatment of a bone disease. Furthermore, the triple agonist or a long-acting conjugate thereof greatly helps in the prevention and/or treatment of a bone disease, such as preventing a bone disease and/or significantly reducing the symptoms of a bone disease, by delaying the relapse of the bone disease.

The composition of the present invention can be used in the prevention or treatment of a bone disease, and especially, can be used in a bone disease caused by an imbalance between osteoblasts and osteoclasts, without limitation. Examples of the "bone disease" may include osteoporosis, fracture, osteosclerosis, osteopetrosis, arthritis, Paget's disease, periodontal disease, osteogenesis imperfecta, and osteopenia, but are not limited thereto.

More specific types of osteoporosis may include primary type 1 osteoporosis, primary type 2 osteoporosis, secondary osteoporosis, osteomalacia-like osteoporosis, osteoporosis due to menopause or ovarian resection, but are not particularly limited thereto.

As used herein, the term "prevention or treatment of bone diseases" encompasses prevention and complete or partial treatment of the bone metabolic disease, especially, osteopenia. The term also encompasses any change in the patients that reduces or alleviates symptoms of bone diseases, relieves pains of the symptoms, reduces the incidence of bone diseases, and increases the outcome of treatment.

The bone resorption by osteoclasts and bone formation by osteoblasts occur repeatedly in combination in the process of bone metabolism, through which the body's mineral balance and bone remodeling occur. For the accurate diagnosis of bone metabolic disease, a need for non-invasive biochemical markers that can accurately evaluate the rates of bone resorption and bone formation comparatively is required in addition to the currently used bone biopsy for the accurate diagnosis of bone metabolic disease. Therefore, osteocalcin (OCN), total and bone-specific alkaline phosphatase (ALP), and the like for markers indicating bone formation, and urinary Ca/Cr ratios, hydroxyproline, pyridinoline (PYD), deoxypyridinoline (DPD), and the like for biochemical markers reflecting bone resorption are being developed and used for biochemical markers of bone metabolism.

Bone remodeling is a process in which old bones are periodically converted into new bones, and this process is performed by stages of proliferation, differentiation, induction of extracellular matrix calcification, and the like. In general, bone formation and resorption in adults are balanced by the interaction between osteoblasts derived from mesenchymal stem cells and osteoclasts derived from hematopoietic stem cells, thereby maintaining bone health. However, an imbalance occurring between these osteoblasts and osteoclasts may cause a metabolic bone disease, such as osteoporosis. The osteoblast differentiation is regulated by various growth factors, cytokines, and gene expression, and has unique characteristics according to the culture method. That is, osteoblasts undergo proliferation, differentiation, and calcification, and trait expressing genes, such as alkaline phosphatase (ALP), type I collagen (Col 1), osteopontin (OPN), and osteocalcin (OCN), are expressed.

The important signaling systems involved in differentiation and bone formation of osteoblasts are known to typically include transforming growth factor-β (TGF-β), bone morphogenetic protein (BMP), Wnt/β-catenin, fibroblast growth factor (FGF), Hedgehog, Notch, and the like. These signaling systems provoke expression and activation of various transcription factors associated with bone formation, such as runt-related transcription factor 2 (Runx2), Osterix, Msh homeobox (Msx), and Distallessrelated homeobox (Dix), during osteoblast differentiation. Inhibitors of DNA binding/differentiation (Ids) are known to be the most important transcription factor observed in various types of cells among target genes of BMP.

As used herein, the term "osteoporosis", which is the most common metabolic disease, refers to a disease in which an imbalance between bone formation and bone resorption causes no change in the bone chemical composition, but reduces the bony quantity in the unit volume and thus the spine, hipbone, and femoral bones are easily fractured. Specifically, osteoporosis is a condition in which the compact bone becomes thinner as the calcified bone tissue density decreases and thus the bone-marrow cavity becomes larger. Therefore, as the condition develops, the bones become fragile and are thus prone to fracture even with a small impact, and osteoporosis is characterized by abnormal bone turnover in which bone resorption and bone turnover are imbalanced. The bone quantity is affected by various factors, such as genetics, nutrition intake, changes in hormone levels, differences in exercise and lifestyle, and the like, and the causes of osteoporosis are known to be aging, insufficient exercise, being underweight, smoking, low-calcium dietary intake, menopause, ovariectomy, or the like. Meanwhile, people of African descent have lower bone resorption levels and thus higher bone quantity than people of European descent although there may be individual differences, and in most cases, bone quantity is highest between the ages of 14 and 18 years and decreases by about 1% per year in the old. In particular, the bone reduction occurs continuously from the age of 30 in women and is accelerated due to hormone changes after menopause. In other words, estrogen levels are rapidly decreased in the menopause, and in particular, as if by interleukin-7 (IL-7), a large number of B-lymphocytes are formed to lead to the accumulation of pre-B cells in the bone marrow, resulting in an increase in the level of IL-6, which enhances the activity of osteoclasts, thereby reducing bone quantity.

As used herein, the term "fracture" refers to a break of a bone, with abnormal disruption of the continuity of a bone, epiphyseal plate or articular surface. The fracture is caused by trauma from traffic accidents and the like, safety accidents in industrial settings, bone changes due to diseases, such as osteoporosis, bone cancer, metabolic disorders, and repetitive stress on bones from sports or weights. The fractures are classified into fissured fractures, greenstick fractures, transverse fractures, oblique fractures, spiral fractures, segmental fractures, comminuted fractures, avulsion fractures, compression fractures, depressed fractures, and the like according to fracture line (line along epiphyseal ends generated upon fracture).

As used herein, the term "osteosclerosis" refers to a disease in which most of the bone tissue is abnormally dense and the bone-marrow cavity is narrowed.

As used herein, the term "osteopetrosis" refers to a disease caused by the dysfunction of osteoclasts for bone resorption, wherein despite an increase in bone mass, the impairment of bone modeling and remodeling may cause easily fragile bones, a reduction in hematopoietic cells, irregular tooth eruption, and growth troubles.

As used herein, the term "arthritis" refers to a disease in which inflammatory changes occur in a joint, and examples thereof may include osteoarthritis, rheumatoid arthritis, and the like.

As used herein, the term "Paget's disease" refers to a localized bone disorder in which bone remodeling is excessively stimulated to invade a wide area of the skeletal system. The pathologic mechanism of Paget's disease is known to be a combination of an excessive increase in bone resorption by osteoclasts with bone cleaning ability and an increase in new bone formation by osteoblasts with bone-forming functions as a compensation thereto, wherein newly formed bones in Paget's disease are structurally disordered and are very vulnerable to bone deformation and fracture. Patients with Paget's disease of bone may be asymptomatic or may be accompanied by various symptoms. Patients with Paget's disease of bone may suffer from direct complications due to the invasion of bone tissue and secondary complications due to the expansion of bone tissue and resulting compression to surrounding nervous tissue.

As used herein, the term "periodontal disease" refers to an inflammatory state of supportive tissue caused by bacteria, and may be classified into gingivitis and periodontitis. The cause of the disease is that dental plaque is formed by oral bacteria due to poor oral hygiene. The dental plaque refers to a mass of bacteria that grow after adhering to a tooth surface using a sticky substance in the saliva as an adhesive. If left untreated, the dental plaque becomes inflamed and sometimes causes bleeding from gums and bad breath, and these symptoms are called gingivitis. As the gingivitis progresses further, the gap between the teeth and the gums becomes deeper, developing into a paradental cyst, where bacteria causing periodontal diseases then multiply to result in periodontitis. As periodontitis progresses, even weak stimuli such as brushing may cause bleeding, and the gums are swelling, often turning into acute inflammation to cause pains. This inflammation impairs bone formation and increases bone resorption, resulting in a reduction in alveolar bone height, and thus the alveolar bone is destroyed, eventually a tooth loss. Therefore, the composition according to the present invention can be advantageously used in the periodontal disease, especially loss of alveolar bone due to periodontal disease.

As used herein, the term "osteogenesis imperfecta" refers to a disease called imperfect osteogenesis, wherein bone strength is weak and thus easily fractured without any particular reason.

As used herein, the term "osteopenia" refers to a condition in which bones are weakened or bone mineral density (BDM) is lower than normal.

The composition of the present invention can prevent or treat a bone disease by performing one or more of the following characteristics when administered to a subject, but is not limited thereto:

(i) reducing serum osteocalcin levels; or (ii) increasing serum procollagen I intact N-terminal propeptide (PINP) levels.

The serum osteocalcin level is a marker for bone resorption, wherein a large amount of osteocalcin in the blood means a lot of bone degradation. The serum PINP level is a marker for bone formation, wherein a high content of PINP means smooth bone formation. These levels may be measured as concentrations in serum, but is not limited thereto. The composition of the present invention, compared with non-administration control groups, can show an effect of preventing or treating a bone disease by reducing serum osteocalcin levels and/or increasing serum PINP levels to thereby perform a mechanism of reducing bone degradation and/or increasing bone formation, but is not limited thereto.

The composition of the present invention can prevent or treat a bone disease by performing one or more of the following characteristics, but is not limited thereto:

(i) increasing osteoblast differentiation; or (ii) increasing viability of osteoblasts.

Osteoblasts are cells involved in bone formation, and an increase in osteoblast differentiation and/or an increase in osteoblast viability means an increase in bone formation. The increase in osteoblast differentiation may be determined by the concentration of collagen, while the viability of osteoblasts may be determined by the luminescence degree according to the ATP level in viable cells, but is not limited thereto. The composition of the present invention, compared with a non-administration control group, can show an effect of preventing or treating a bone disease by increasing osteoblast differentiation and/or increasing osteoblast viability to thereby increasing bone formation and/or reducing bone formation due to nutrient deficiency, but is not limited thereto.

The pharmaceutical composition of the present invention may further contain a pharmaceutically acceptable carrier, vehicle, or diluent. The pharmaceutically acceptable carrier, vehicle, or diluent may be non-naturally occurring.

As used herein, the term "pharmaceutically acceptable" refers to the amount enough to show therapeutic effects, without causing side effects, and such an amount can be easily determined by a person skilled in the art depending the factors well-known in a medical field, such as the type of disease, patient's age, weight, health, and sex, patient's sensitivity to drugs, route of administration, method of administration, frequency of administration, duration of treatment, drugs used in combination or concurrently.

The pharmaceutical composition containing the peptide of the present invention may further contain a pharmaceutically acceptable vehicle. With respect to the vehicle, although not particularly limited, but a binder, a lubricant, a disintegrant, a solubilizer, a dispersant, a stabilizer, a suspending agent, a coloring agent, a flavoring agent, and the like may be used for oral administration; a buffer, a preservative, an analgesic, a solubilizer, an isotonic agent, a stabilizer, and the like may be mixed for an injection; and a base, a vehicle, a lubricant, a preservative, and the like may be used for topical administration.

The formulation of the composition of the present invention may be prepared in various manners by mixing with the above-described pharmaceutically acceptable vehicle. For example, for oral administration, the composition of the present invention may be formulated in the form of a tablet, a troche, a capsule, an elixir, a suspension, a syrup, a wafer, or the like; for the injection, the composition may be formulated as a single dose ampoule or a multi-dose form. The composition may be formulated into a solution, a suspension, a tablet, a pill, a capsule, a long-acting preparation, or the like.

Meanwhile, examples of the carrier, vehicle, and diluent suitable for preparation may include lactose, dextrose, sucrose, sorbitol, mannitol, xylitol, erythritol, maltitol, starch, acacia, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oils, and the like. In addition, the composition may further contain a filler, an anti-coagulant, a lubricant, a humectant, a flavoring agent, a preservative, and the like.

In addition, the pharmaceutical composition of the present invention may have any one formulation selected from the group consisting of a tablet, a pill, a powder, granules, a capsule, a suspension, a liquid medicine for internal use, an emulsion, a syrup, a sterile aqueous solution, a non-aqueous solvent, a lyophilized preparation, and a suppository.

The composition may be formulated into a single dose form suitable for the patient's body, and specifically, may be formulated into a preparation useful for the administration of a protein drug, and may be administered by an administration method commonly used in the art through an oral or parenteral route, such as through a skin, intravenous, intramuscular, intra-arterial, intramedullary, intrathecal, intraventricular, pulmonary, transdermal, subcutaneous, intraperitoneal, intranasal, intragastric, topical, sublingual, vaginal, or rectal route, but is not limited thereto.

In addition, the conjugate may be used by mixing with various carriers approved as drugs, such as physiological saline or organic solvents, and for increasing stability or absorptivity, carbohydrates such as glucose, sucrose, or dextran, antioxidants such as ascorbic acid or glutathione, chelating agents, low-molecular weight proteins, or other stabilizers may be used as medical agents.

The dose and frequency of the pharmaceutical composition of the present invention are determined according to the type of drug as an active ingredient, together with various factors, such as a disease to be treated, a route of administration, patient's age, gender, and body weight, and severity of a disease. Specifically, the composition of the present invention may contain a pharmaceutically effective amount of the peptide or the long-acting conjugate containing the peptide, but is not limited thereto.

Containing the peptide or the long-acting conjugate in a pharmaceutically effective amount means a level at which desired pharmaceutical activity (e.g., prevention, alleviation, or treatment of a bone disease) can be obtained by the peptide or a long-acting conjugate thereof, and may also mean a level at which toxicities or side effects are absent or present at a slight level as a pharmaceutically acceptable level in a subject to be administered, but the level is not limited thereto. Such a pharmaceutically effective amount may be determined by comprehensively considering the frequency of administration, patient, formulation, and the like.

Although not particularly limited, the pharmaceutical composition of the present invention may contain the ingredient (active ingredient) in an amount of 0.01 to 99% (w/v).

The total effective amount of the composition of the present invention may be administered to a patient in a single dose, or may be administered in multiple doses by a fractionated treatment protocol for a long period of time. The pharmaceutical composition of the present invention may an active ingredient, of which the content may vary depending on the severity of a disease. Specifically, the preferable total dose of the triple agonist or a long-acting conjugate thereof of the present invention may be about 0.0001 to 500 mg per 1 kg of body weight of a patient per day. However, as for the dose of the triple agonist or a long-acting conjugate thereof, the effective does thereof for a patient is determined considering various factors including patient's age, body weight, health condition, and sex, the severity of a disease, a diet, and a rate of excretion, in addition to the route of administration and the frequency of treatment of the pharmaceutical composition, and thus, considering these, a person skilled in the art may easily determine an appropriate effective dose according to the particular use of the composition of the present invention. The pharmaceutical composition according to the present invention is not particularly limited to the formulation, route of administration, and method of administration, as long as the pharmaceutical composition exhibits the effects of the present invention.

The pharmaceutical composition of the present invention has excellent in vivo duration of efficacy and potency, thereby significantly reducing the number and frequency of administration of the pharmaceutical preparation of the present invention.

In accordance with another aspect of the present invention, there is provided a food composition for preventing or treating a bone disease, the food composition containing the triple agonist (peptide) and/or a long-acting conjugate of the triple agonist.

The peptide, conjugate, bone disease, and others are as described above.

The food composition may be used as a health functional food. When the composition of the present invention is used as a food additive, the peptide (the peptide itself or a long-acting conjugate thereof) may be added as it is, or may be used along with other food or food ingredients, and may be appropriately used by a conventional method. The amount of the active ingredient mixed may be properly determined according to the purpose of use (prevention, health, or therapeutic treatment).

As used herein, the term "health functional food" refers to a food that is manufactured and processed by using a particular ingredient as a raw material or by extraction, concentration, purification, or mixing of a particular ingredient contained in a food raw material, for the purpose of assisting the health care, wherein the health functional food indicates food that is designed and processed so as to sufficiently exert, on biological bodies, bio-regulatory functions, such as biodefense, biorhythm regulation, prevention and recovery of a diseases, and the like by the above ingredient. The composition for health food may perform functions associated with prevention of a disease and the recovery of the disease.

In accordance with another aspect of the present invention, there is provided a method for preventing or treating a bone disease, the method including administering to a subject in need thereof the triple agonist (peptide) or a long-acting conjugate of the triple agonist or a composition containing the peptide or the long-acting conjugate.

The triple agonist and/or a long-acting conjugate of the triple agonist, or the composition containing the same, the bone metabolic disease, and the like are as described above.

The subject refers to a subject suspected of having a bone disease, and the subject suspected of having a bone disease indicates mammals including humans, rats, livestock, and the like, which have or are at the risk of developing the corresponding disease, but any subject that can be treated with the peptide and/or conjugate or the composition containing the same is included without limitation.

As used herein, the term "administration" refers to the introduction of a predetermined substance into a patient by any appropriate method, and the route of administration of the composition may include, but is not particularly limited to, any typical route through which the composition can arrive at a target in vivo, and for example, the route of administration may be intraperitoneal administration, intravenous administration, intramuscular administration, subcutaneous administration, intradermal administration, oral administration, topical administration, intranasal administration, intrapulmonary administration, intrarectal administration, or the like.

The method of the present invention may include administering a pharmaceutically effective amount of the pharmaceutical composition containing the peptide or the conjugate thereof. The appropriate total daily dose of the pharmaceutical composition may be determined by a practitioner within the scope of correct medical decision, and the pharmaceutical composition may be administered once or several times in divided doses. For the purpose of the present invention, the specific therapeutically effective dose for a specific patient may be preferably applied differently, depending on various factors well known in the medical art, including the type and degree of response to be achieved, a specific composition including whether other agents are occasionally used therewith or not, the patient's age, body weight, general health condition, sex and a diet, the time of administration, the route of administration, the secretion rate of the composition, the duration of treatment, other drugs used in combination or concurrently with the composition of the present invention, and like factors well-known in the medical art.

In accordance with another aspect of the present invention, there is provided use of a composition containing the triple agonist peptide or a long-acting conjugate of the peptide in the preparation of a medicine for prevention or treatment of a bone disease.

The peptide and/or conjugate, the composition containing the same, the bone disease, and the prevention and treatment thereof are as described above.

In accordance with another aspect of the present invention, there is provided use of a peptide and/or conjugate or a composition containing the same for preventing or treating a bone disease.

The peptide and/or conjugate, the composition containing the same, the bone disease, and the prevention and treatment thereof are as described above.

Hereinafter, the present invention will be described in detail with reference to the following examples. However, the following examples are merely for illustrating the present invention and are not intended to limit the scope of the present invention.

Example 1: Preparation of Triple Agonists

Triple agonists showing activities for all of GLP-1, GIP, and glucagon receptors were prepared, and amino acid sequences thereof are shown in Table 1 below.

TABLE 1

| SEQ ID NO | Sequence | Information |
|---|---|---|
| 1 | HXQGTFTSDVSSYLDGQAAKEFIAWLVKGC | |
| 2 | HXQGTFTSDVSSYLDGQAQKEFIAWLVKG C | |
| 3 | HXQGTFTSDVSSYLLGQAAKQFIAWLVKGG GPSSGAPPPSC | |
| 4 | HXQGTFTSDVSSYLLGQQQKEFIAWLVKG C | |
| 5 | HXQGTFTSDVSSYLLGQQQKEFIAWLVKG GGPSSGAPPPSC | |
| 6 | HXQGTFTSDVSSYLDGQAAKEFVAWLLKG C | |
| 7 | HXQGTFTSDVSKYLDGQAAKEFVAWLLKG C | |
| 8 | HXQGTFTSDVSKYLDGQAAQEFVAWLLKG C | |
| 9 | HXQGTFTSDVSKYLDGQAAQEFVAWLLAG C | |
| 10 | HXQGTFTSDVSKYLDGQAAQEFVAWLLAG GGPSSGAPPPSC | |
| 11 | CAGEGTFTSDLSKYLDSRRQQLFVQWLKAG GPSSGAPPPSHG | |
| 12 | CAGEGTFISDLSKYMDEQAVQLFVEWLMAG GPSSGAPPPSHG | |
| 13 | CAGEGTFISDYSIQLDEIAVQDFVEWLLAQK PSSGAPPPSHG | |

TABLE 1-continued

| SEQ ID NO | Sequence | Information |
|---|---|---|
| 14 | CAGQGTFTSDYSIQLDEIAVRDFVEWLKNG GPSSGAPPPSHG | |
| 15 | CAGQGTFTSDLSKQMDEEAVRLFIEWLKNG GPSSGAPPPSHG | |
| 16 | CAGQGTFTSDLSKQMDSEAQQLFIEWLKNG GPSSGAPPPSHG | |
| 17 | CAGQGTFTSDLSKQMDEERAREFIEWLLAQ KPSSGAPPPSHG | |
| 18 | CAGQGTFTSDLSKQMDSERAREFIEWLKNT GPSSGAPPPSHG | |
| 19 | CAGQGTFTSDLSIQYDSEHQRDFIEWLKDT GPSSGAPPPSHG | |
| 20 | CAGQGTFTSDLSIQYEEEAQQDFVEWLKDT GPSSGAPPPSHG | |
| 21 | YXQGTFTSDYSKYLDECRAKEFVQWLLDH HPSSGQPPPS | Ring formation |
| 22 | YXQGTFTSDYSKCLDEKRAKEFVQWLLDH HPSSGQPPPS | Ring formation |
| 23 | YXQGTFTSDYSKYLDECRAKEFVQWLLAQK GKKNDWKHNIT | Ring formation |
| 24 | YXQGTFTSDYSKYLDECRAKEFVQWLKNG GPSSGAPPPS | Ring formation |
| 25 | HXQGTFTSDCSKYLDERAAQDFVQWLLDG GPSSGAPPPS | |
| 26 | HXQGTFTSDCSKYLDSRAAQDFVQWLLDG GPSSGAPPPS | |
| 27 | HXQGTFTSDYSKYLDERACQDFVQWLLDQ GGPSSGAPPPS | |
| 28 | HXQGTFTSDYSKYLDEKRAQEFVCWLLAQ KGKKNDWKHNIT | |
| 29 | HXQGTFTSDYSKYLDEKAAKEFVQWLLNTC | Ring formation |
| 30 | HXQGTFTSDYSKYLDEKAQKEFVQWLLDT C | Ring formation |
| 31 | HXQGTFTSDYSKYLDEKACKEFVQWLLAQ | Ring formation |
| 32 | HXQGTFTSDYSKYLDEKACKDFVQWLLDG GPSSGAPPPS | Ring formation |
| 33 | HXQGTFTSDYSIAMDEIHQKDFVNWLLAQ KC | Ring formation |
| 34 | HXQGTFTSDYSKYLDEKRQKEFVNWLLAQ KC | Ring formation |
| 35 | HXQGTFTSDYSIAMDEIHQKDFVNWLLNTK C | Ring formation |
| 36 | HXQGTFTSDYSKYLCEKRQKEFVQWLLNG GPSSGAPPPSG | Ring formation |
| 37 | HXQGTFTSDYSKYLDECRQKEFVQWLLNG GPSSGAPPPSG | Ring formation |
| 38 | CAXQGTFTSDKSSYLDERAAQDFVQWLLDG GPSSGAPPPSS | |
| 39 | HXQGTFTSDYSKYLDGQHAQCFVAWLLAG GGPSSGAPPPS | |

TABLE 1-continued

| SEQ ID NO | Sequence | Information |
|---|---|---|
| 40 | HXQGTFTSDKSKYLDERACQDFVQWLLDG GPSSGAPPPS | |
| 41 | HXQGTFTSDKSKYLDECAAQDFVQWLLDG GPSSGAPPPS | |
| 42 | YXQGTFTSDYSKYLDEKRAKEFVQWLLDH HPSSGQPPPSC | Ring formation |
| 43 | YXQGTFTSDYSKYLDEKRAKEFVQWLLDH HCSSGQPPPS | Ring formation |
| 44 | HGQGTFTSDCSKQLDGQAAQEFVAWLLAG GPSSGAPPPS | |
| 45 | HGQGTFTSDCSKYMDGQAAQDFVAWLLAG GPSSGAPPPS | |
| 46 | HGQGTFTSDCSKYLDEQHAQEFVAWLLAG GPSSGAPPPS | |
| 47 | HGQGTFTSDCSKYLDGQRAQEFVAWLLAG GPSSGAPPPS | |
| 48 | HGQGTFTSDCSKYLDGQRAQDFVNWLLAG GPSSGAPPPS | |
| 49 | CAXQGTFTSDYSICMDEIHQKDFVNWLLNT K | Ring formation |
| 50 | HXQGTFTSDYSKYLDEKRAKEFVQWLLDH HPSSGQPPPSC | Ring formation |
| 51 | HXQGTFTSDYSKYLDEKRQKEFVQWLLNT C | Ring formation |
| 52 | HXQGTFTSDYSKYLDEKRQKEFVQWLLDT C | Ring formation |
| 53 | HXEGTFTSDYSIAMDEIHQKDFVNWLLAQC | Ring formation |
| 54 | HXEGTFTSDYSIAMDEIHQKDFVDWLLAEC | Ring formation |
| 55 | HXQGTFTSDYSIAMDEIHQKDFVNWLLAQC | Ring formation |
| 56 | HXQGTFTSDYSKYLDEKRQKEFVNWLLAQ C | Ring formation |
| 57 | HXQGTFTSDYSIAMDEIHQKDFVNWLLNTC | Ring formation |
| 58 | HXQGTFTSDYSKYLDEKRQKEFVQWLLNT KC | Ring formation |
| 59 | CAXQGTFTSDYSICMDEKHQKDFVNWLLNT K | Ring formation |
| 60 | CAXQGTFTSDYSIAMDEKHCKDFVNWLLNT K | Ring formation |
| 61 | CAXQGTFTSDYSIAMDEIACKDFVNWLLNT K | Ring formation |
| 62 | CAXQGTFTSDKSKYLDERAAQDFVQWLLDG GPSSGAPPPS | |
| 63 | CAXQGTFTSDCSKYLDERAAQDFVQWLLDG GPSSGAPPPS | |
| 64 | YXQGTFTSDYSKYLDECAAKEFVQWLLDHH PSSGQPPPS | Ring formation |
| 65 | HXQGTFTSDYSKCLDEKRAKEFVQWLLDH HPSSGQPPPS | Ring formation |

TABLE 1-continued

| SEQ ID NO | Sequence | Information |
|---|---|---|
| 66 | YXQGTFTSDYSKYLDECRAKDFVQWLLDH HPSSGQPPPS | Ring formation |
| 67 | YXQGTFTSDYSKYLDECAAKDFVQWLLDH HPSSGQPPPS | Ring formation |
| 68 | YXQGTFTSDYSKCLDEKAAKEFVQWLLDH HPSSGQPPPS | Ring formation |
| 69 | YXQGTFTSDYSKCLDERAAKEFVQWLLDH HPSSGQPPPS | Ring formation |
| 70 | YXQGTFTSDYSKCLDEKRAKDFVQWLLDH HPSSGQPPPS | Ring formation |
| 71 | YXQGTFTSDYSKYLDERACKDFVQWLLDH HPSSGQPPPS | Ring formation |
| 72 | YXQGTFTSDCSKYLDERAAKDFVQWLLDH HPSSGQPPPS | Ring formation |
| 73 | CAXQGTFTSDYSKYLDECRAKEFVQWLLDH HPSSGQPPPS | Ring formation |
| 74 | CAXQGTFTSDYSKCLDEKRAKEFVQWLLDH HPSSGQPPPS | Ring formation |
| 75 | YXQGTFTSDYSKYLDEKAAKEFVQWLLDHH PSSGQPPPSC | Ring formation |
| 76 | YXQGTFTSDYSKYLDEKRAKDFVQWLLDH HPSSGQPPPSC | Ring formation |
| 77 | YXQGTFTSDYSKYLDEKAAKDFVQWLLDHH PSSGQPPPSC | Ring formation |
| 78 | HXQGTFTSDYSKYLDEKRQKEFVQWLLDT KC | Ring formation |
| 79 | HXEGTFTSDYSIAMDEIHQKDFVNWLLAQK C | Ring formation |
| 80 | HXEGTFTSDYSIAMDEIHQKDFVDWLLAEK C | Ring formation |
| 81 | CAXQGTFTSDYSKYLDEKRQKEFVQWLLNT C | Ring formation |
| 82 | CAXQGTFTSDYSKYLDEKRQKEFVQWLLDT C | Ring formation |
| 83 | CAXEGTFTSDYSIAMDEIHQKDFVNWLLAQ C | Ring formation |
| 84 | CAXEGTFTSDYSIAMDEIHQKDFVDWLLAE C | Ring formation |
| 85 | CAXQGTFTSDYSIAMDEIHQKDFVNWLLAQ C | Ring formation |
| 86 | CAXQGTFTSDYSKYLDEKRQKEFVNWLLAQ C | Ring formation |
| 87 | CAXQGTFTSDYSIAMDEIHQKDFVNWLLNT C | Ring formation |
| 88 | CAXQGTFTSDYSKYLDEKRQKEFVQWLLNT KC | Ring formation |
| 89 | CAXQGTFTSDYSKYLDEKRQKEFVQWLLDT KC | Ring formation |
| 90 | CAXEGTFTSDYSIAMDEIHQKDFVNWLLAQ KC | Ring formation |
| 91 | CAXEGTFTSDYSIAMDEIHQKDFVDWLLAE KC | Ring formation |

TABLE 1-continued

| SEQ ID NO | Sequence | Information |
|---|---|---|
| 92 | CAXQGTFTSDYSIAMDEIHQKDFVNWLLAQ KC | Ring formation |
| 93 | CAXQGTFTSDYSKYLDEKRQKEFVNWLLAQ KC | Ring formation |
| 94 | CAXQGTFTSDYSIAMDEIHQKDFVNWLLNT KC | Ring formation |
| 95 | YXQGTFTSDYSKYLDEKRAKEFVQWLLCH HPSSGQPPPS | Ring formation |
| 96 | YXQGTFTSDYSKYLDEKRAKEFVQWLLDH CPSSGQPPPS | Ring formation |
| 97 | YXQGTFTSDYSKYLDEKRAKEFVQWLLDC HPSSGQPPPS | Ring formation |
| 98 | YXQGTFTSDYSKALDEKAAKEFVNWLLDHH PSSGQPPPSC | Ring formation |
| 99 | YXQGTFTSDYSKALDEKAAKDFVNWLLDHH PSSGQPPPSC | Ring formation |
| 100 | YXQGTFTSDYSKALDEKAAKEFVQWLLDQH PSSGQPPPSC | Ring formation |
| 101 | YXQGTFTSDYSKALDEKAAKEFVNWLLDQH PSSGQPPPSC | Ring formation |
| 102 | YXQGTFTSDYSKALDEKAAKDFVNWLLDQH PSSGQPPPSC | Ring formation |

In the sequences shown in Table 1, the amino acid marked with X represents 2-aminoisobutyric acid (Aib), which is a non-native amino acid, and the underlined amino acids represent amino acids forming a ring together. In Table 1, CA represents 4-imidazoacetyl. The triple agonist peptides were used as triple agonist having the amidated C-terminus, as needed.

Example 2: Preparation of Long-Acting Conjugates of Triple Agonists

To PEGylate cysteine residues of the triple agonists (SEQ ID NOS: 21, 22, 42, 43, 50, 77, and 96) of Example 1 with PEG (10 kDa) with a maleimide group and an aldehyde group at both ends, respectively, that is, maleimide-PEG-aldehyde (10 kDa, NOF, Japan), the triple agonists and the maleimide-PEG-aldehyde were reacted at a molar ratio of 1:1-3, a protein concentration of 1 to 5 mg/ml, and a low temperature, for 0.5 to 3 hours. The reaction was conducted under an environment in which 20-60% isopropanol was added to 50 mM Tris buffer (pH 7.5). Upon completion of the reaction, the reaction solutions were applied to SP Sepharose HP (GE healthcare, USA) to purify triple agonist having mono-PEGylated cysteine.

Then, the purified mono-PEGylated triple agonists and an immunoglobulin Fc were reacted at a molar ratio of 1:1-5, a protein concentration of 10-50 mg/ml, and 4 to 8° C. for 12 to 18 hours. The reaction was conducted in an environment in which 10-50 mM sodium cyanoborohydride as a reducing agent and 10-30% isopropanol were added to 100 mM potassium phosphate buffer (pH 6.0). Upon completion of the reaction, the reaction solutions were applied to the butyl sepharose FF purification column (GE healthcare, USA) and Source ISO purification column (GE healthcare, USA) to purify conjugates including the triple agonists and immunoglobulin Fc. The purified long-acting conjugates have a structure in which a triple agonist peptide, a polyethylene glycol (PEG) linker, and an Fc dimer are covalently linked at a molar ratio of 1:1:1, wherein the PEG linker is linked to only one of the two polypeptide chains of the Fc dimer.

In the immunoglobulin Fc, two monomers having the amino acid sequence of SEQ ID NO: 123 (consisting of 221 amino acids) form a homodimer through an inter-disulfide bond between cysteines, which are the 3rd amino acids of the respective monomers, wherein the monomers of the homodimer independently form an inter-disulfide bond between the cysteines at positions 35 and 95 and an inter-disulfide bond between the cysteines at positions 141 and 199, respectively.

The purity of the conjugates that was analyzed by reverse-phase chromatography, size exclusion chromatography, and ion exchange chromatography after the preparation was 95% or more.

In particular, a conjugate in which a triple agonist, obtained by amidation of the C-terminus of the triple agonist of SEQ ID NO: 21, is bound to the immunoglobulin Fc via PEG was named "conjugate including SEQ ID NO: 21 and immunoglobulin Fc", "long-acting conjugate of SEQ ID NO: 21", or "SEQ ID NO: 21 long-acting conjugate", and these may be used interchangeably herein.

In particular, a conjugate in which a triple agonist, obtained by amidation of the C-terminus of the triple agonist of SEQ ID NO: 22, is bound to the immunoglobulin Fc via PEG was named "conjugate including SEQ ID NO: 22 and immunoglobulin Fc", "long-acting conjugate of SEQ ID NO: 22", or "SEQ ID NO: 22 long-acting conjugate", and these may be used interchangeably herein.

In particular, a conjugate in which a triple agonist, obtained by amidation of the C-terminus of the triple agonist of SEQ ID NO: 42, is bound to the immunoglobulin Fc via PEG was named "conjugate including SEQ ID NO: 42 and immunoglobulin Fc", "long-acting conjugate of SEQ ID NO: 42", or "SEQ ID NO: 44 long-acting conjugate", and these may be used interchangeably herein.

In particular, a conjugate in which a triple agonist, obtained by amidation of the C-terminus of the triple agonist of SEQ ID NO: 43, is bound to the immunoglobulin Fc via PEG was named "conjugate including SEQ ID NO: 43 and immunoglobulin Fc", "long-acting conjugate of SEQ ID NO: 43", or "SEQ ID NO: 43 long-acting conjugate", and these may be used interchangeably herein In particular, a conjugate in which a triple agonist, obtained by amidation of the C-terminus of the triple agonist of SEQ ID NO: 50, is bound to the immunoglobulin Fc via PEG was named "conjugate including SEQ ID NO: 50 and immunoglobulin Fc", "long-acting conjugate of SEQ ID NO: 50", or "SEQ ID NO: 50 long-acting conjugate", and these may be used interchangeably herein.

In particular, a conjugate in which a triple agonist, obtained by amidation of the C-terminus of the triple agonist of SEQ ID NO: 77, is bound to the immunoglobulin Fc via PEG was named "conjugate including SEQ ID NO: 77 and immunoglobulin Fc", "long-acting conjugate of SEQ ID NO: 77", or "SEQ ID NO: 77 long-acting conjugate", and these may be used interchangeably herein In particular, a conjugate in which a triple agonist, obtained by amidation of the C-terminus of the triple agonist of SEQ ID NO: 96, is bound to the immunoglobulin Fc via PEG was named "conjugate including SEQ ID NO: 96 and immunoglobulin Fc", "long-acting conjugate of SEQ ID NO: 96", or "SEQ ID NO: 21 long-acting conjugate", and these may be used interchangeably herein.

Experimental Example 1: In Vitro Activities of Triple Agonists and Long-Acting Conjugates Thereof To measure the activities of the triple agonists and the long-acting conjugates thereof prepared in Examples 1 and 2, a method of measuring cell activity in vitro was employed by using cell lines in which GLP-1, glucagon (GCG), and GIP receptors were transformed, respectively.

The cell lines were obtained by transforming Chinese hamster ovary (CHO) cells to express human GLP-1 receptor, human GCG receptor, and human GIP receptor, respectively, and these cell lines were suitable for the measurement of the activities of GLP-1, GCG, and GIP. Therefore, the activities for the receptors were measured using the transformed cell lines, respectively.

For the measurement of the GLP-1 activity of the triple agonists and the long-acting conjugates thereof prepared in Examples 1 and 2, human GLP-1 was subjected to serial dilution, and the triple agonists and the long-acting conjugates thereof prepared in Examples 1 and 2 were subjected to serial dilution. The cultures were removed from the cultured CHO cells expressing the human GLP-1 receptor, and 5 μL of each of the continuously diluted materials was added to the cells, and then 5 μL of a cAMP antibody-containing buffer was added, followed by incubation at room temperature for 15 minutes. Then, 10 μL of a detection mix containing a cell lysis buffer was added to lyse the cells, followed by incubation at room temperature for 90 minutes. The cell lysates upon completion of the reaction were applied to the LANCE cAMP kit (PerkinElmer, USA) to calculate $EC_{50}$ values through accumulated cAMP, and then the values were compared with each other. The relative potency ratios compared with human GLP-1 are shown in Tables 2 and 3 below.

For the measurement of the GCG activity of the triple agonists and the long-acting conjugates thereof prepared in Examples 1 and 2, human GCG was subjected to serial dilution, and the triple agonists and the long-acting conjugates thereof prepared in Examples 1 and 2 were subjected to serial dilution. The cultures were removed from the cultured CHO cells expressing the human GCG receptor, and 5 μL of each of the continuously diluted materials was added to the cells, and then 5 μL of a cAMP antibody-containing buffer was added, followed by incubation at room temperature for 15 minutes. Then, 10 μL of a detection mix containing a cell lysis buffer was added to lyse the cells, followed by incubation at room temperature for 90 minutes. The cell lysates upon completion of the reaction were applied to the LANCE cAMP kit (PerkinElmer, USA) to calculate $EC_{50}$ values through accumulated cAMP, and then the values were compared with each other. The relative potency ratios compared with human GCG are shown in Tables 2 and 3 below.

For the measurement of the GIP activity of the triple agonists and the long-acting conjugates thereof prepared in Examples 1 and 2, human GIP was subjected to serial dilution, and the triple agonists and the long-acting conjugates thereof prepared in Examples 1 and 2 were subjected to serial dilution. The cultures were removed from the cultured CHO cells expressing the human GIP receptor, and 5 μL of each of the continuously diluted materials was added to the cells, and then 5 μL of a cAMP antibody-containing buffer was added, followed by incubation at room temperature for 15 minutes. Then, 10 μL of a detection mix containing a cell lysis buffer was added to lyse the cells, followed by incubation at room temperature for 90 minutes. The cell lysates upon completion of the reaction were applied to the LANCE cAMP kit (PerkinElmer, USA) to calculate $EC_{50}$ values through accumulated cAMP, and then the values were compared with each other. The relative potency ratios compared with human GIP are shown in Tables 2 and 3 below.

TABLE 2

Relative potency ratios of triple agonists

| SEQ ID NO | In vitro activity (%) compared with native peptide vs GLP-1 | vs Glucagon | vs GIP |
|---|---|---|---|
| 1 | 3.2 | <0.1 | <0.1 |
| 2 | 5.9 | <0.1 | <0.1 |
| 3 | 1.8 | <0.1 | <0.1 |
| 4 | 8.5 | <0.1 | <0.1 |
| 5 | 42.1 | <0.1 | <0.1 |
| 6 | 17.0 | <0.1 | <0.1 |
| 7 | 13.7 | <0.1 | <0.1 |
| 8 | 14.2 | 0.10 | <0.1 |
| 9 | 32.1 | 0.13 | <0.1 |
| 10 | 46.0 | <0.1 | <0.1 |
| 11 | 1.4 | <0.1 | <0.1 |
| 12 | 0.4 | <0.1 | <0.1 |
| 13 | <0.1 | <0.1 | <0.1 |
| 14 | 28.0 | <0.1 | <0.1 |
| 15 | 79.2 | <0.1 | <0.1 |
| 16 | 2.1 | <0.1 | <0.1 |
| 17 | 0.2 | <0.1 | <0.1 |
| 18 | <0.1 | <0.1 | <0.1 |
| 19 | <0.1 | <0.1 | <0.1 |
| 20 | <0.1 | <0.1 | <0.1 |
| 21 | 17.8 | 267 | 22.7 |

TABLE 2-continued

Relative potency ratios of triple agonists

| SEQ ID NO | In vitro activity (%) compared with native peptide vs GLP-1 | vs Glucagon | vs GIP |
|---|---|---|---|
| 22 | 20.1 | 140 | 59.7 |
| 23 | 4.01 | 9.3 | <0.1 |
| 24 | 41.2 | 9.3 | <0.1 |
| 25 | 82.6 | 0.1 | <0.1 |
| 26 | 64.5 | 0.2 | <0.1 |
| 27 | 83.1 | 0.8 | 0.9 |
| 28 | 17.2 | 1.6 | <0.1 |
| 29 | 38.5 | 6.0 | <0.1 |
| 30 | 142 | 0.7 | 0.8 |
| 31 | 135 | 2.2 | 2.4 |
| 32 | 151 | 1.7 | 8.8 |
| 33 | 24.5 | <0.1 | 10.4 |
| 34 | 19.1 | 0.92 | 0.6 |
| 35 | 7.5 | <0.1 | 1.3 |
| 36 | 37.4 | 0.39 | 0.2 |
| 37 | 236 | 6.21 | 2.2 |
| 38 | 2.3 | — | — |
| 39 | 13.9 | 0.53 | <0.1 |
| 40 | 75.2 | <0.1 | <0.1 |
| 41 | 34.3 | <0.1 | <0.1 |
| 42 | 33.9 | 205.8 | 7.8 |
| 43 | 12.6 | 88.4 | 3.70 |
| 44 | 1.3 | <0.1 | <0.1 |
| 45 | 6.6 | <0.1 | <0.1 |
| 46 | 1.4 | <0.1 | <0.1 |
| 47 | 2.4 | <0.1 | <0.1 |
| 48 | 1.5 | <0.1 | <0.1 |
| 49 | 29.8 | <0.1 | 3.3 |
| 50 | 67.4 | 50.5 | 2.7 |
| 51 | 14.4 | 2.0 | 0.1 |
| 52 | 44.1 | 7.5 | 0.3 |
| 53 | 161 | 8.4 | 1.3 |
| 54 | 30.6 | 1.4 | 0.1 |
| 55 | 27.1 | 0.7 | 2.4 |
| 56 | 57.9 | 4.9 | 0.8 |
| 57 | 11.7 | <0.1 | 0.3 |
| 58 | 39.1 | 2.6 | 0.2 |
| 59 | 40.3 | <0.1 | 4.0 |
| 60 | 106.2 | <0.1 | 8.2 |
| 61 | 59.8 | <0.1 | 2.8 |
| 62 | 5.2 | <0.1 | <0.1 |
| 63 | 15.3 | <0.1 | <0.1 |
| 64 | 64.6 | 60.1 | 92.9 |
| 65 | 95.4 | 25.2 | 11.6 |
| 66 | 15.8 | 172 | 17.2 |
| 67 | 28.5 | 46.2 | 39.8 |
| 68 | 27.9 | 8.8 | 107 |
| 69 | 24.3 | 9.6 | 62.8 |
| 70 | 15.1 | 71.3 | 64.4 |
| 71 | 90.1 | 12.7 | 94.7 |
| 72 | 11.5 | 1.0 | 1.6 |
| 73 | 22.6 | 5.4 | 3.0 |
| 74 | 12.9 | 0.9 | 1.0 |
| 75 | 35.1 | 8.5 | 18.0 |
| 76 | 10.3 | 47.6 | 11.7 |
| 77 | 38.7 | 12.2 | 35.5 |
| 78 | 51.0 | 14.0 | 0.12 |
| 79 | 41.5 | 4.9 | 1.4 |
| 80 | 8.1 | 0.0 | 0.1 |
| 81 | 7.8 | 0.3 | <0.1 |
| 82 | 9.5 | 1.1 | <0.1 |
| 83 | 47.3 | 1.3 | 0.4 |
| 84 | 4.2 | <0.1 | <0.1 |
| 85 | 4.3 | <0.1 | 0.3 |
| 86 | 28.4 | 0.4 | 0.2 |
| 87 | 0.9 | <0.1 | <0.1 |
| 88 | 9.6 | 0.3 | <0.1 |
| 89 | 7.1 | 0.7 | <0.1 |
| 90 | 7.4 | <0.1 | <0.1 |
| 91 | 31.9 | 16.8 | 0.3 |
| 92 | 0.8 | <0.1 | 0.4 |
| 93 | 5.7 | 0.3 | 0.7 |
| 94 | 0.5 | <0.1 | <0.1 |
| 95 | 2.1 | 0.4 | <0.1 |
| 96 | 34.4 | 194.8 | 5.2 |
| 97 | 10.5 | 62.8 | 2.6 |
| 98 | 28.1 | 8.2 | 47.1 |
| 99 | 20.9 | 14.9 | 57.7 |
| 100 | 42.2 | 12.7 | 118.5 |
| 101 | 23.2 | 13.9 | 40.1 |
| 102 | 23.3 | 29.5 | 58.0 |

TABLE 3

Relative potency ratios of long-acting conjugates of triple agonists

| Long-acting conjugates | In vitro activity (%) compared with native peptide vs GLP-1 | vs Glucagon | vs GIP |
|---|---|---|---|
| SEQ ID NO: 21 long-acting conjugate | 0.1 | 1.6 | 0.2 |
| SEQ ID NO: 22 long-acting conjugate | 0.1 | 0.9 | 0.5 |
| SEQ ID NO: 42 long-acting conjugate | 3.1 | 23.1 | 1.2 |
| SEQ ID NO: 43 long-acting conjugate | 2.1 | 13.5 | 0.6 |
| SEQ ID NO: 50 long-acting conjugate | 15.4 | 6.9 | 0.7 |
| SEQ ID NO: 77 long-acting conjugate | 6.7 | 1.7 | 6.6 |
| SEQ ID NO: 96 long-acting conjugate | 0.3 | 4.0 | 0.3 |

The long-acting conjugates of triple agonists prepared above have the function as a triple agonist, which can activate all of GLP-1, GIP, and glucagon receptors, and thus can be used as a therapeutic substance for a target disease.

Experimental Example 2: Changes in Serum Osteocalcin Level and Serum PINP Level in Osteoporosis Model Rats According to Administration of Long-Acting Conjugate of Triple Agonist The therapeutic effect of the triple agonist of the present invention was examined in an osteoporosis animal model, which is a representative bone disease model experimentally induced. The long-acting conjugate of the triple agonist of SEQ ID NO: 42 (long-acting conjugate of SEQ ID NO: 42) was selected as a representative example of a long-acting conjugate of a triple agonist and then experimented.

Specifically, in order to assess the in vivo effect according to the administration of a composition containing the long-acting conjugate of the triple agonist prepared in Example 2, ovariectomized rats (OVX rats, Orient Inc. Korea) as an osteoporosis model were used. The ovariectomized rats were used in the present experiment example since the rats had osteoporosis symptoms due to a lack of ovarian hormones resulting from ovary removal.

Six-week-old female Sprague-Dawley rats were ovariectomized and then subjected to osteoporosis induction for 12 weeks. The degree of induction of osteoporosis was determined by comparing the serum osteocalcin level between normal rats and ovariectomized rats. Five female rats were assigned to a normal group (G1), and groups with osteoporosis induced through ovariectomy were divided into four groups G2, G3, G4, and G5, with seven rats in each group.

The groups were classified into a normal control group without administration (Vehicle), an ovariectomized control group without administration after ovariectomy (OVX vehicle), and groups administered liraglutide (25 nmol/kg/BID), the long-acting conjugate of SEQ ID NO: 42 (2.2 nmol/kg/Q3D), and the long-acting conjugate of SEQ ID NO: 42 (4.4 nmol/kg/Q3D). The test substance was repeatedly administered for 4 weeks, and then each of the groups was measured for serum osteocalcin levels and serum procollagen I intact N-terminal propeptide (PINP) levels. The serum osteocalcin level is a marker for bone resorption, wherein a large amount of osteocalcin in the blood means a lot of bone degradation. The serum PINP level is a marker for bone formation, wherein a high content of PINP in the blood means smooth bone formation.

As a test result, compared with the ovariectomized control group, the groups administered the long-acting conjugate of the triple agonist showed a dose-dependent reduction in serum osteocalcin level (FIG. 2) and a dose-dependent increase in serum PINP level (FIG. 1). These results indicate remarkable improvements even compared with the liraglutide administration group. Statistical analysis was performed by one-way ANOVA to compare between the ovariectomized control group and the test groups.

These results indicate that the administration of the long-acting conjugate of the triple agonist of the present invention exhibited excellent effect of preventing or treating bond metabolic diseases including osteoporosis through bone degradation reducing and bone formation increasing mechanisms.

Experimental Example 3: Effect of Increasing Osteoblast Differentiation and Cell Viability of MC3T3-E1 Osteoblasts by Treatment with Long-Acting GLP-1/Glucagon/GIP Triple Conjugate The therapeutic effect of the triple agonist of the present invention was examined. The long-acting conjugate of the triple agonist of SEQ ID NO: 42 (long-acting conjugate of SEQ ID NO: 42) was selected as a representative example of a long-acting conjugate of a triple agonist and then experimented.

Specifically, MC3T3-E1 osteoblasts were used to measure in vitro effects of increasing osteoblast differentiation and changing osteoblast viability according to the treatment with a composition containing the long-acting conjugate of SEQ ID NO: 42 prepared in Example 2.

Test methods and results on <Effect of increasing differentiation of MC3T3-E1 osteoblasts by treatment with long-acting GLP-1/Glucagon/GIP triple conjugate> and <Effect of increasing viability of MC3T3-E1 osteoblasts by treatment with long-acting GLP-1/Glucagon/GIP triple conjugate> are as follows.

(1) Effect of Increasing Differentiation of MC3T3-E1 Osteoblasts by Treatment with Long-Acting GLP-1/Glucagon/GIP Triple Conjugate To examine the effect of inducing osteoblast differentiation by the treatment with the long-acting conjugate of SEQ ID NO: 42 prepared in Example 2, the changes in RUNX2, OCN, ColA1, and ALP, which are major markers involved in differentiation, were examined at the mRNA level.

MC3T3-E1 osteoblasts were dispensed into 12-well plates at 100,000 cells/well and incubated for 24 hours using a medium containing 10% fetal bovine serum. Thereafter, the cells were divided into a normal control group not treated with the long-acting conjugate of SEQ ID NO: 42, a test group treated with the long-acting conjugate of SEQ ID NO: 42 (1 μM), and a test group treated with the long-acting conjugate of SEQ ID NO: 42 (10 μM), which were then induced to differentiate for 72 hours.

After 72 hours, RNA was harvested using RNA extraction kit (Qiagen), and cDNA was synthesized using cDNA synthesis kit (Biorad). RT-PCR was performed using the synthesized cDNA. RT-PCR was performed by the following particular primers.

```
RUNX2
Forward primer:
                                    (SEQ ID NO: 124)
5'-GCCCTCATCCTTCACTCCAAG-3'

Reverse primer:
                                    (SEQ ID NO: 125)
5'-GGTCAGTCAGTGCCTTTCCTC-3'

OCN
Forward primer:
                                    (SEQ ID NO: 126)
5'-GAGGGCAATAAGGTAGTGAA-3'

Reverse primer:
                                    (SEQ ID NO: 127)
5'-CATAGATGCGTTTGTAGGC-3'

ALP
Forward primer:
                                    (SEQ ID NO: 128)
5'-CCAGCAGGTTTCTCTCTTGG-3'

Reverse primer:
                                    (SEQ ID NO: 129)
5'-GGAATGTTCCATGGAGGTTG-3'

ColA1
Forward primer:
                                    (SEQ ID NO: 130)
5'-AGAGCATGACCGATGGATTC-3'

Reverse primer:
                                    (SEQ ID NO: 131)
5'-CCTTCTTGAGGTTGCCAGTC-3'

GAPDH
Forward primer:
                                    (SEQ ID NO: 132)
5'-GTCGTGGATCTGACGTGCC-3'

Reverse primer:
                                    (SEQ ID NO: 133)
5'-TGCCTGCTTCACCACCTTC-3'
```

As shown in the test results (FIG. 3), the treatment with the long-acting conjugate of SEQ ID NO: 42 increased the mRNA expression levels of RUNX2, OCN, ALP, and ColA1, which were osteoblast differentiation genes, in a dose-dependent manner. Statistical analysis was performed by one-way ANOVA to compare between the control group and the test groups.

Subsequently, the influence of the treatment with the long-acting conjugate of SEQ ID NO: 42 on the production of ColA1, a major marker for osteoblast differentiation, was examined at the protein level.

MC3T3-E1 osteoblasts were dispensed into 12-well plates at 100,000 cells/well and incubated for 24 hours using a medium containing 10% fetal bovine serum. Thereafter, the cells were divided into a normal control group not treated with the long-acting conjugate of SEQ ID NO: 42, a test group treated with the long-acting GIP (1 μM), a test group treated with the long-acting conjugate of SEQ ID NO: 42 (1

μM), a test group treated with the long-acting conjugate of SEQ ID NO: 42 (10 μM), and a test group treated with the long-acting conjugate of SEQ ID NO: 42 (1 μM or 10 μM) or a GIP inhibitor (10 μM or 100 μM), and further incubated for 7 days. The long-acting GIP used in the present invention was prepared by the same method as in the long-acting conjugate of the triple agonist illustrated in Example 2, wherein the long-acting GIP is in a form in which immunoglobulin Fc was linked to GIP analog via PEG, and the GIP inhibitor is GIP 3-30, in which the N-terminus was absent in native GIP.

After 7 days, the incubated medium was collected, and ColA1 in the medium was quantified using a collagen assay kit (Biocolor) according to the manufacturer's instructions.

As shown in the test results (FIG. 4), ColA1 protein was increased by the treatment with the long-acting conjugate of SEQ ID NO: 42 as well as long-acting GIP in a dose-dependent manner, and the effect of the long-acting conjugate of SEQ ID NO: 42 on the expression of ColA1 protein was reduced by GIP inhibitor. Statistical analysis was performed by one-way ANOVA to compare between the control group and the test groups.

These results indicate that the long-acting conjugate of SEQ ID NO: 42 of the present invention can exhibit excellent effect of preventing osteoporosis through the bone formation accelerating mechanism and the GIP activity of the long-acting conjugate of SEQ ID NO: 42 plays an important role in this mechanism.

(2) Effect of Increasing Viability of MC3T3-E1 Osteoblasts by Treatment with Long-Acting GLP-1/Glucagon/GIP Triple Conjugate To measure the viability of osteoblasts by the treatment with the long-acting conjugate of SEQ ID NO: 42 prepared in Example 2, the luminescence degree according to the ATP level of viable cell was measured using CellTiter-Glo (Promega).

MC3T3-E1 osteoblasts were dispensed into 96-well plates at 10,000 cells/well and incubated for 24 hours using a medium containing 10% fetal bovine serum. The medium in a normal group was replaced with a medium containing 10% bovine fetal serum, and the medium in each of the test groups was replaced with a medium containing no bovine fetal serum. The test groups were divided into a test group not treated with the long-acting conjugate of SEQ ID NO: 42, the test group treated with the long-acting conjugate of SEQ ID NO: 42 (2 μM), and the test groups co-treated with the long-acting conjugate of SEQ ID NO: 42 (2 μM) and the GIP inhibitor (0.31 μM, 1.25 μM, 5 μM, and 20 μM, respectively). The medium in each of the normal group and test groups was replaced, and after 48 hours, the cells were further incubated. Thereafter, the cell viability was analyzed using a collagen assay kit (Biocolor) according to the manufacturers instructions. The GIP inhibitor is GIP 3-30, in which the N-terminus region was absent in native GIP.

As a test result, the cell viability was greatly reduced in the test groups not treated with the long-acting conjugate of SEQ ID NO: 42, compared with the normal control group. The results confirmed that the cell viability reduced due to deficiency in bovine fetal serum was increased by the treatment with the long-acting conjugate of SEQ ID NO: 42, and the cell viability increased by the long-acting conjugate of SEQ ID NO: 42 was reduced by GIP inhibitor in a dose-dependent manner (FIG. 5). Statistical analysis was performed by one-way ANOVA to compare between the test group not treated with the long-acting conjugate of SEQ ID NO: 42 and the test groups co-treated with the long-acting conjugate of SEQ ID NO: 42 (2 μM) and the GIP inhibitor (0.31 μM, 1.25 μM, 5 μM, and 20 μM, respectively).

These results indicate that the GIP activity retained in the long-acting conjugate of SEQ ID NO: 42 can exhibit an effect of preventing osteoporosis due to a deficiency in nutrients through the cell viability increasing mechanism.

The above results support that the triple agonists and/or conjugates thereof of the present invention were effective in bone formation and thus can prevent or treat various bone diseases associated with bone reduction, and therefore, the triple agonists and/or conjugates thereof can be provided as new medicines for bone diseases.

While the present invention has been described with reference to the particular illustrative embodiments, a person skilled in the art to which the present invention pertains can understand that the present invention may be embodied in other specific forms without departing from the technical spirit or essential characteristics thereof. In this regard, the embodiments described above should be understood to be illustrative rather than restrictive in every respect. The scope of the invention should be construed that the meaning and scope of the appended claims rather than the detailed description and all changes or variations derived from the equivalent concepts fall within the scope of the present invention.

The invention claimed is:

1. A method for treatment of a bone disease of a subject in need thereof, comprising administering to the subject a pharmaceutical composition comprising:

a pharmaceutically acceptable vehicle; and a therapeutically effective amount of a peptide containing an amino acid sequence of any one of SEQ ID NOS: 21, 22, 30-32, 34, 36, 37, 42, 43, 50-56, 58, 64-79, 83, 86, 91, 93 and 96-102, wherein the bone disease is selected from the group consisting of osteoporosis, osteosclerosis, osteopetrosis, Paget's disease, osteogenesis imperfecta, and osteopenia.

2. The method according to claim 1, wherein the peptide is in the form of a long-acting conjugate, and the long-acting conjugate is represented by Formula 1 below:

X-L-F [Formula 1]

wherein X represents a peptide containing an amino sequence of any one of SEQ ID NOS: 21, 22, 30-32, 34, 36, 37, 42, 43, 50-56, 58, 64-79, 83, 86, 91, 93 and 96-102;

L represents a linker containing ethylene glycol repeat units;

F represents an immunoglobulin Fc region; and

"-" symbols represent covalent linkages between X and L and between L and F, respectively.

3. The method according to claim 1, wherein the peptide contains an amino acid sequence selected from the group consisting of SEQ ID NOS: 21, 22, 42, 43, 50, 64, 66, 67, 70, 71, 76, 77, 96, 97, and 100.

4. The method according to claim 3, wherein the peptide contains an amino acid sequence selected from the group consisting of SEQ ID NOS: 21, 22, 42, 43, 50, 66, 67, 77, 96, 97, and 100.

5. The method according to claim 4, wherein the peptide contains an amino acid sequence selected from the group consisting of SEQ ID NOS: 21, 22, 42, 43, 50, 77, and 96.

6. The method according to claim 1, wherein the amino acids at positions 16 and 20 from the N-terminus in the sequence of the peptide form a ring.

7. The method according to claim 1, wherein the C-terminus of the peptide is amidated.

8. The method according to claim 2, wherein L is polyethylene glycol.

9. The method according to claim 2, wherein the formula weight of the ethylene glycol repeat units in L is in a range of 1 to 100 kDa.

10. The method according to claim 2, wherein the immunoglobulin Fc region is aglycosylated.

11. The method according to claim 2, wherein F is an IgG Fc region.

12. The method according to claim 2, wherein the immunoglobulin Fc region is a dimer consisting of two polypeptide chains, and one end of L is linked only to one of the two polypeptide chains.

13. The method according to claim 2, wherein in the conjugate, one end of L is linked to F via a covalent linkage formed by reaction with an amine or thiol group of F, and the other end of L is linked to X via a covalent linkage formed by reaction with an amine or thiol group of X.

14. The method according to claim 1, further comprising measuring, after administering the pharmaceutical composition, a serum osteocalcin level and/or a serum procollagen I intact N-terminal propeptide (PINP) level in the subject, wherein, compared with a control group not administered with the pharmaceutical composition, the administering results in one or both of:

(i) reducing the serum osteocalcin level; and (ii increasing the serum PINP level.

15. The method according to claim 1, further comprising evaluating osteoblast differentiation and/or osteoblast viability after administering the pharmaceutical composition, wherein:

(i) the osteoblast differentiation is determined based on a collagen concentration in an osteoblast assay; and/or (ii) the osteoblast viability is determined based on a luminescence degree according to an ATP level in viable cells in an osteoblast assay, and wherein, compared with a control group not administered with the pharmaceutical composition, the administering results in one or both of:

(i) increasing osteoblast differentiation; and (ii) increasing viability of osteoblasts.

16. The method according to claim 1, wherein the bone disease is osteoporosis.

17. The method of claim 16, wherein the osteoporosis is postmenopausal osteoporosis or osteoporosis caused by ovarian hormone deficiency.

* * * * *